United States Patent
Pindiprolu et al.

(10) Patent No.: US 9,951,599 B2
(45) Date of Patent: Apr. 24, 2018

(54) DETERMINING SURFACE WETTING OF METAL WITH CHANGING WELL FLUIDS

(71) Applicant: Halliburton Energy Services, Inc., Houston, TX (US)

(72) Inventors: Sairam KS Pindiprolu, Pune (IN); Dennis Willie Gray, Comanche, OK (US); Venkata Gopala Rao Palla, Pune (IN)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/922,520

(22) Filed: Oct. 26, 2015

(65) Prior Publication Data

US 2016/0047221 A1 Feb. 18, 2016

Related U.S. Application Data

(62) Division of application No. 13/596,598, filed on Aug. 28, 2012, now Pat. No. 9,200,491.

(51) Int. Cl.

| | |
|---|---|
| *G01V 3/00* | (2006.01) |
| *E21B 47/00* | (2012.01) |
| *E21B 21/00* | (2006.01) |
| *G01V 3/18* | (2006.01) |
| *G01N 13/00* | (2006.01) |
| *E21B 33/14* | (2006.01) |
| *G01N 27/02* | (2006.01) |

(52) U.S. Cl.
CPC .............. *E21B 47/00* (2013.01); *E21B 21/00* (2013.01); *E21B 33/14* (2013.01); *G01N 13/00* (2013.01); *G01N 27/026* (2013.01); *G01V 3/18* (2013.01)

(58) Field of Classification Search
CPC .......................................................... G01V 3/04
USPC .......................................................... 324/347
See application file for complete search history.

(56) References Cited

U.S. PATENT DOCUMENTS

| | | | |
|---|---|---|---|
| 4,557,142 A | 12/1985 | Hensley et al. | |
| H0001932 H * | 1/2001 | Heathman et al. | ...... 166/250.14 |
| 6,988,547 B2 * | 1/2006 | Goodwin et al. | ............... 166/53 |
| 2002/0170341 A1 | 11/2002 | Jakoby et al. | |
| 2006/0070426 A1 | 4/2006 | Pelletier | |

(Continued)

FOREIGN PATENT DOCUMENTS

CN 101196460 A 6/2008

OTHER PUBLICATIONS

International Search Report and Written Opinion issued in related PCT Application No. PCT/US2013/049648, dated Nov. 13, 2013, 8 pages.

(Continued)

*Primary Examiner* — Bot Ledynh
(74) *Attorney, Agent, or Firm* — John W. Wustenberg; Baker Botts L.L.P.

(57) ABSTRACT

Methods and apparatuses for determining surface wetting of a metallic material with changing well fluids. In general, the methods according to the invention include measuring electrical impedance spectroscopy ("EIS") for a system simulating downhole conditions for the wetting of a surface. Methods and apparatuses for making EIS measurements model double-layer capacitance at a downhole surface in a well, from which the nature and quantification of the wetting of the surface can be inferred.

19 Claims, 19 Drawing Sheets

(56) References Cited

U.S. PATENT DOCUMENTS

| | | | |
|---|---|---|---|
| 2008/0163703 A1 | 7/2008 | Boncan et al. | |
| 2009/0184003 A1* | 7/2009 | Hammonds et al. | 205/775.5 |
| 2011/0005310 A1 | 1/2011 | Lunkad et al. | |
| 2011/0061451 A1 | 3/2011 | Harris et al. | |
| 2011/0198078 A1 | 8/2011 | Harrigan et al. | |
| 2011/0251795 A1 | 10/2011 | DiFoggio | |
| 2012/0048008 A1 | 3/2012 | Pindiprolu et al. | |

OTHER PUBLICATIONS

International Preliminary Report on Patentability issued in related PCT Application No. PCT/US2013/049648 dated Mar. 12, 2015, 7 pages.

International Search Report and Written Opinion issued in related PCT Application No. PCT/US2013/049637, dated Oct. 10, 2013, 7 pages.

International Preliminary Report on Patentability issued in related PCT Application No. PCT/US2013/049637, dated Mar. 12, 2015, 6 pages.

Extended European Search Report issued in related EU application No. 13833515 dated Mar. 2, 2016, 9 pages.

Maurer, W. C. et al : "Development and Testing of Underbalanced Drilling Products", internet citation, Jul. 2001 (Jul. 2001), XP002361847, Retrieved from the Internet: URL:http://www.osti.gov/servlets/purl/8206 13-qHnN Ei /native/Appendi x H, p. 218-p. 222; figures 1-4.

US Statutory Invention Registration No. H1932 H published Jan. 2, 2001, by Heathman, et al.

N Bona et al: "Advances in understanding the relationship between rock wettability and high-frequency dielectric response" Journal of Petroleum Science and Engineering, vol. 33, No. 1-3, Apr. 1, 2002, pp. 87-99, XP055245952, NL ISSN: 0920-4105, DOI: 10.1016/S0920-4105(01)00178-4.

Extended European Search Report issued in related EU application No. 13833956 dated Apr. 8, 2016, 10 pages.

\* cited by examiner

DETERMINING SURFACE WETTING OF METAL WITH CHANGING WELL FLUIDS

CROSS-REFERENCE TO RELATED APPLICATIONS

This application is a divisional of application Ser. No. 13/596,598, filed Aug. 28, 2012, which is incorporated herein by reference in its entirety.

TECHNICAL FIELD

The inventions are in the field of producing crude oil or natural gas from subterranean formations. More specifically, the inventions generally relate to methods and apparatuses for determining surface wetting with changing of well fluids. Applications of the methods and apparatuses include without limitation, for example, the designing of spacer or inverter fluids and the field-operational parameters for wellbore cleanout and fluid separation prior to cementing operations in a well.

BACKGROUND ART

To produce oil or gas, a well is drilled into a subterranean formation that is an oil or gas reservoir.

Well Servicing and Well Fluids

Generally, well services include a wide variety of operations that may be performed in oil, gas, geothermal, or water wells, such as drilling, cementing, completion, and intervention. Well services are designed to facilitate or enhance the production of desirable fluids such as oil or gas from or through a subterranean formation. A well service usually involves introducing a well fluid into a well.

Drilling is the process of drilling the wellbore. After a portion of the wellbore is drilled, sections of steel pipe, referred to as casing, which are slightly smaller in diameter than the borehole, are placed in at least the uppermost portions of the wellbore. The casing provides structural integrity to the newly drilled borehole.

Cementing is a common well operation. For example, hydraulic cement compositions can be used in cementing operations in which a string of pipe, such as casing or liner, is cemented in a wellbore. The cement stabilizes the pipe in the wellbore and prevents undesirable migration of fluids along the annulus between the wellbore and the outside of the casing or liner from one zone along the wellbore to the next. Where the wellbore penetrates into a hydrocarbon-bearing zone of a subterranean formation, the casing can later be perforated to allow fluid communication between the zone and the wellbore. The cemented casing also enables subsequent or remedial separation or isolation of one or more production zones of the wellbore, for example, by using downhole tools such as packers or plugs, or by using other techniques, such as forming sand plugs or placing cement in the perforations. Hydraulic cement compositions can also be utilized in intervention operations, such as in plugging highly permeable zones or fractures in zones that may be producing too much water, plugging cracks or holes in pipe strings, and the like.

Completion is the process of making a well ready for production or injection. This principally involves preparing a zone of the wellbore to the required specifications, running in the production tubing and associated downhole equipment, as well as perforating and stimulating as required.

Intervention is any operation carried out on a well during or at the end of its productive life that alters the state of the well or well geometry, provides well diagnostics, or manages the production of the well. Workover can broadly refer to any kind of well intervention that involves invasive techniques, such as wireline, coiled tubing, or snubbing. More specifically, however, workover usually refers to a process of pulling and replacing a completion.

Drilling and Drilling Fluids

The well is created by drilling a hole into the earth (or seabed) with a drilling rig that rotates a drill string with a drilling bit attached to the downward end. Usually the borehole is anywhere between about 5 inches (13 cm) to about 36 inches (91 cm) in diameter. As upper portions are cased or lined, progressively smaller drilling strings and bits must be used to pass through the uphole casings or liners, which steps the borehole down to progressively smaller diameters.

While drilling an oil or gas well, a drilling fluid is circulated downhole through a drillpipe to a drill bit at the downhole end, out through the drill bit into the wellbore, and then back uphole to the surface through the annular path between the tubular drillpipe and the borehole. The purpose of the drilling fluid is to maintain hydrostatic pressure in the wellbore, lubricate the drill string, and carry rock cuttings out from the wellbore.

The drilling fluid can be water-based or oil-based. Oil-based fluids tend to have better lubricating properties than water-based fluids, nevertheless, other factors can mitigate in favor of using a water-based drilling fluid. Such factors may include but not limited to presence of water-swellable formations, need for a thin but a strong and impermeable filtercake, temperature stability, corrosion resistance, stuck pipe prevention, contamination resistance and production protection.

Cementing and Hydraulic Cement Compositions

Hydraulic cement is a material that when mixed with water hardens or sets over time because of a chemical reaction with the water. The cement composition sets by a hydration process, passing through a gel phase to solid phase. Because this is a chemical reaction with water, hydraulic cement is capable of setting even under water.

The hydraulic cement, water, and any other components are mixed to form a hydraulic cement composition in fluid form. The hydraulic cement composition is pumped as a fluid (typically in the form of suspension or slurry) into a desired location in the wellbore. For example, in cementing a casing or liner, the hydraulic cement composition is pumped into the annular space between the exterior surfaces of a pipe string and the borehole (that is, the wall of the wellbore). The hydraulic cement composition should be a fluid for a sufficient time before setting to allow for pumping the composition into the wellbore and for placement in a desired downhole location in the well. The cement composition is allowed time to set in the annular space, thereby forming an annular sheath of hardened, substantially impermeable cement. The hardened cement supports and positions the pipe string in the wellbore and fills the annular space between the exterior surfaces of the pipe string and the borehole of the wellbore.

Wettability and Wetting of Solid Surfaces

The wettability of a solid surface or a film on a solid surface can impact various well applications. For example, an oleaginous film on a metal surface of a tubular or a rock material of a subterranean formation can affect bonding of hydraulic cement to the surface. The wettability of rock or the wetting of the rock can affect the flow of a fluid through the matrix of rock of a subterranean formation.

Wettability involves the contact between a liquid and a solid surface, resulting from the intermolecular interactions when the two different phases are brought together. In general, the degree of wetting (wettability) is depends on a force balance between adhesive forces between the liquid and solid surface and cohesive forces of the liquid (i.e., surface tensions). Adhesive forces between a liquid and solid cause a liquid drop to spread across the surface. Cohesive forces within the liquid cause the drop to ball up and avoid contact with the surface.

A measurement of the degree of wettability is the contact angle, the angle at which the liquid interface meets the dry solid interface. If the wettability is very favorable to the liquid, the contact angle will be low, and the fluid will spread to cover or "wet" a larger area of the solid surface. If the wettability is unfavorable, the contact angle will be high, and the fluid will form a compact, self-contained droplet on the solid surface. If the contact angle of a water droplet on a solid surface is less than 90°, the surface may be said to be "water-wettable" (and inverse proportionally, probably not oil-wettable); whereas if the contact angle of an oil droplet on a solid surface is less than 90°, the surface may be said to be "oil-wettable" (and inverse proportionally, not water-wettable. The surfaces of some materials are both water wettable and oil wettable.

TABLE 1

| Surface Tension of a liquid | Adhesion of the liquid to solid surface | Contact Angle | Degree of Wettability |
|---|---|---|---|
| Weak | Strong | $\theta = 0°$ | Theoretically perfectly wettable |
| Strong | Strong | $0° < \theta < 90°$ | High wettability |
| Weak | Weak | $0° < \theta < 90°$ | High wettability |
| Strong | Weak | $90° \leq \theta < 180°$ | Low wettability |
| Strong | Weak | $\theta = 180°$ | Theoretically perfectly non-wettable |

As used herein, a wet or wetted surface or the wetting of a surface may refer to a liquid phase that is directly in contact with and adhered to the surface of a solid body. For example, the liquid phase can be an oleaginous film on the surface of a metallic tubular or the face of a borehole in the material of a subterranean formation.

Some well fluids can form such a film or layer on a downhole surface, which can have undesirable effects. The fluid (or a liquid component of the fluid) can form a film or layer on the surface, which can act as a physical barrier between the material of the underlying solid body and a fluid adjacent to the surface of the solid body. In effect, such a film presents a different wettability characteristic than the material of the underlying solid body. For example, an oleaginous film on the surface of a metal tubular blocks water from wetting the underlying surface, which would otherwise be water-wettable.

A metallic surface of a downhole tubular is typically both water wettable and oil wettable. If first wetted with an oleaginous film, however, the oleaginous film on the metallic surface blocks the metal surface from being wettable with a water-based fluid.

Wetting of Tubulars and Formation Surfaces for Cementing

Hydraulic cement compositions do not bond well to oil-wetted surfaces. After drilling a wellbore with an oil-based drilling mud, the surfaces of tubulars and the formation in the wellbore may become oil-wetted with an oleaginous film. It is necessary to remove the film on the solid surface of the tubular from being oil-wetted with such a film to improve cement bonding.

In a case where complete surface wetting with water is not achieved prior to placing cement in the desired zone of interest, only partial bonding of the surfaces with cement is obtained. Because of this incomplete surface bonding, there is a proportional decrease in the shear bond strength of the interface between the set cement sheath and the formation/tubular surfaces and premature interfacial de-bonding might occur under the loads experienced during the course of the well operations. This may have unwanted consequences such as interzonal communication, loss of production, and sustained casing pressure. Any of these can be detrimental to the safety and economics of hydrocarbon production from the well.

Significance of Interfacial Phenomena

Physical, chemical, and electrical properties of matter confined to phase boundaries are often profoundly different from those of the same matter in bulk. For many systems, although multiphase, the fraction of total mass localized at the phase boundaries is small that the contribution of such boundary properties to the general system properties is negligible.

However, many important systems exist under which these properties play significant role. For example, such systems include dispersions in liquids, which can be of solids (e.g., sols, suspensions, or slurries) or of other liquids (e.g., emulsions). In dispersions, the phase boundary area is so large relative to the volume of the system that a substantial fraction of the total mass of the system is present at the boundaries. Surfactants (also known as surface-active agents) play a major role in these systems.

Another such system is where the phenomena occurring at the phase boundaries are so different from the bulk phases that the behavior of the system is substantially determined by phase-boundary processes. Examples include detergency, floatation, and cleanout.

It is necessary to understand the causes of the behavior of matter at the phase-interfaces and the variables that affect this behavior in order to predict and control the properties of systems in which phase-boundary properties play a significant role. In addition, as temperature, pressure, shear, and other conditions vary, these properties used to quantify interfacial phenomena will also change. The systems of well fluids and operations with well fluids can be highly complex and difficult to predict.

It would be highly desirable in well operations to have methods for determining wettability and improving operating conditions and contact times for well fluids. Applications include, for example, the designing of spacer or inverter fluids and determining the field-operational parameters for wellbore cleanout and fluid separation prior to cementing operations in a well.

SUMMARY OF THE INVENTION

According to the invention, methods and apparatuses are provided for determining surface wetting with changing of well fluids. In general, the methods according to the invention include measuring electrical impedance spectroscopy ("EIS") for a system simulating downhole conditions for the wetting of a surface. Methods and apparatuses for making EIS measurements model double-layer capacitance at a downhole surface in a well under the conditions in the well, from which the nature and quantification of the wetting of the surface for such conditions can be inferred.

In addition, methods are provided for making EIS measurements downhole in a well to measure surface wetting directly in the downhole environment and conditions.

These and other aspects of the invention will be apparent to one skilled in the art upon reading the following detailed description. While the invention is susceptible to various modifications and alternative forms, specific embodiments thereof will be described in detail and shown by way of example. It should be understood, however, that it is not intended to limit the invention to the particular forms disclosed, but, on the contrary, the invention is to cover all modifications and alternatives falling within the spirit and scope of the invention as expressed in the appended claims.

BRIEF DESCRIPTION OF THE DRAWING

The accompanying drawing is incorporated into the specification to help illustrate examples according to the presently most-preferred embodiment of the invention.

FIG. 1a illustrates a drilling mud initially the annulus of the wellbore around the casing. FIG. 1b illustrates a spacer fluid being pumped through the casing to displace the drilling mud from the annulus. FIG. 1c illustrates a cement composition (sometimes referred to as a cement slurry) being pumped through the casing to displace the spacer fluid and placed in the annulus for cementing the casing in the wellbore. To seal the annulus with cement requires good cement bonding between both the outer wall of the casing and the rock of the subterranean formation of the borehole.

In FIG. 2, the spacer fluid is illustrated being pumped into the well and down through a casing (which has not yet been cemented) and then out the lower end of the casing and up through the annulus between the outside of the casing and the borehole of the wellbore. As the spacer fluid displaces the prior fluid in the wellbore, there is a diffused layer of mixing and channeling between the prior fluid and the spacer fluid. The diffused layer includes varying mixtures of the prior fluid in the well and spacer fluid. Such a diffused layer is sometimes referred to as contaminated spacer fluid. The spacer fluid being pumped behind the diffused layer is sometimes referred to as pure or uncontaminated spacer fluid.

As illustrated in FIG. 8, in this embodiment the rock surface is axially separated from another electrode exposed to a bulk fluid in the chamber of the container. It should be understood, of course, that the dielectric constant of the insulating material of the container should be higher than that of any liquid phases being tested for wetting on the testing surface. This type of apparatus can measure the change in surface wetting on a tested dielectric surface from a first liquid phase to a second liquid phase as a second bulk fluid including the second liquid phase is sheared in the container of the apparatus at a controlled rate for a controlled contact time. The dielectric solid surfaces can be selected to simulate the rock of a subterranean formation in a well. The first liquid phase can simulate a prior oleaginous film formed on the surface of the rock. The second bulk fluid can and conditions of shear and time can simulate the displacement of the oleaginous film by a spacer fluid.

FIG. 9a is a vertical cross-sectional view of a portion of a metallic tubular, such as a casing, positioned in a wellbore. FIG. 9b is a detail view of a test probe device associated with a portion of the casing in the wellbore.

FIG. 11 is similar to the type of circuit known as a Failed Paint Model (FP) circuit model.

FIG. 12 is similar to the type of circuit known as a Failed Paint Model with Diffusion ("CPED") circuit model.

DETAILED DESCRIPTION OF PRESENTLY PREFERRED EMBODIMENTS AND BEST MODE

Definitions and Usages

Interpretation

Figure 1:
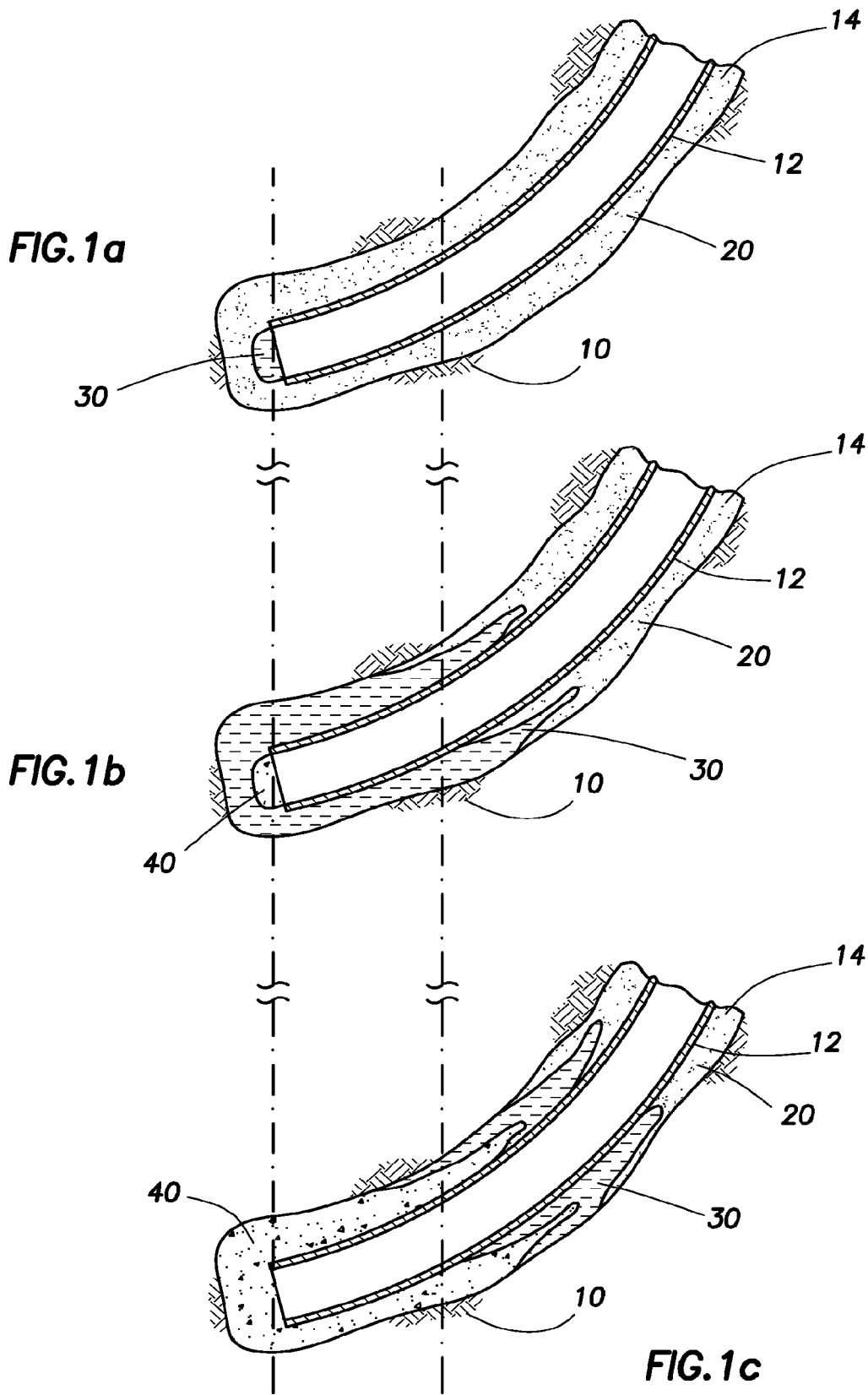
FIGS. 1a, 1b, and 1c are illustrations of a sequence of fluid displacement in a wellbore during a cementing operation. The spacer fluid is illustrated being pumped into a wellbore of a well penetrating a formation 10 and down through a casing (which has not yet been cemented) and then out the lower end of the casing and up through the annulus between the outside of the casing and the borehole of the wellbore.

The words or terms used herein have their plain, ordinary meaning in the field of this disclosure, except to the extent explicitly and clearly defined in this disclosure or unless the specific context otherwise requires a different meaning.

If there is any conflict in the usages of a word or term in this disclosure and one or more patent(s) or other documents that may be incorporated by reference, the definitions that are consistent with this specification should be adopted.

The words "comprising," "containing," "including," "having," and all grammatical variations thereof are intended to have an open, non-limiting meaning. For example, a composition comprising a component does not exclude it from having additional components, an apparatus comprising a part does not exclude it from having additional parts, and a method having a step does not exclude it having additional steps. When such terms are used, the compositions, apparatuses, and methods that "consist essentially of" or "consist of" the specified components, parts, and steps are specifically included and disclosed.

The control or controlling of a condition includes any one or more of maintaining, applying, or varying of the condition. For example, controlling the temperature of a substance can include maintaining an initial temperature, heating, or cooling.

The indefinite articles "a" or "an" mean one or more than one of the component, part, or step that the article introduces.

Whenever a numerical range of degree or measurement with a lower limit and an upper limit is disclosed, any number and any range falling within the range is also intended to be specifically disclosed. For example, every range of values (in the form "from a to b," or "from about a to about b," or "from about a to b," "from approximately a to b," and any similar expressions, where "a" and "b" represent numerical values of degree or measurement) is to be understood to set forth every number and range encompassed within the broader range of values.

Terms such as "first," "second," "third," etc. are assigned arbitrarily and are merely intended to differentiate between two or more components, parts, or steps that are otherwise similar or corresponding in nature, structure, function, or action. For example, the words "first" and "second" serve no other purpose and are not part of the name or description of the following name or descriptive terms. The mere use of the term "first" does not require that there be any "second" similar or corresponding component, part, or step. Similarly, the mere use of the word "second" does not require that there by any "first" or "third" similar or corresponding component, part, or step. Further, it is to be understood that the mere use of the term "first" does not require that the element or step be the very first in any sequence, but merely that it is at least one of the elements or steps. Similarly, the mere use of the terms "first" and "second" does not necessarily require any sequence. Accordingly, the mere use of such terms does not exclude intervening elements or steps between the "first" and "second" elements or steps, etc.

Well Terms

In the context of production from a well, oil and gas are understood to refer to crude oil and natural gas. Oil and gas are naturally occurring hydrocarbons in certain subterranean formations.

A "subterranean formation" is a body of rock that has sufficiently distinctive characteristics and is sufficiently continuous for geologists to describe, map, and name it.

In geology, rock or stone is a naturally occurring solid aggregate of minerals or mineraloids. The Earth's outer solid layer, the lithosphere, is made of rock. Three majors groups of rocks are defined: igneous, sedimentary, and metamorphic.

A subterranean formation having a sufficient porosity and permeability to store and transmit fluids is sometimes referred to as a "reservoir." The vast majority of reservoir rocks are sedimentary rocks, but highly fractured igneous and metamorphic rocks sometimes contain substantial reservoirs as well.

A subterranean formation containing oil or gas may be located under land or under the seabed off shore. Oil and gas reservoirs are typically located in the range of a few hundred feet (shallow reservoirs) to a few tens of thousands of feet (ultra-deep reservoirs) below the surface of the land or seabed.

A "well" includes a wellhead and at least one wellbore from the wellhead penetrating the earth. The "wellhead" is the surface termination of a wellbore, which surface may be on land or on a seabed. A "well site" is the geographical location of a wellhead of a well. It may include related facilities, such as a tank battery, separators, compressor stations, heating or other equipment, and fluid pits. If offshore, a well site can include a platform.

The "wellbore" refers to the drilled hole, including any cased or uncased portions of the well or any other tubulars in the well. The "borehole" usually refers to the inside wellbore wall, that is, the rock surface or wall that bounds the drilled hole. A wellbore can have portions that are vertical, horizontal, or anything in between, and it can have portions that are straight, curved, or branched. As used herein, "uphole," "downhole," and similar terms are relative to the direction of the wellhead, regardless of whether a wellbore portion is vertical or horizontal.

A wellbore can be used as a production or injection wellbore. A production wellbore is used to produce hydrocarbons from the reservoir. An injection wellbore is used to inject a fluid, e.g., liquid water or steam, to drive oil or gas to a production wellbore.

As used herein, introducing "into a well" means introduced at least into and through the wellhead. According to various techniques known in the art, tubulars, equipment, tools, or well fluids can be directed from the wellhead into any desired portion of the wellbore.

As used herein, the word "tubular" means any kind of body in the form of a tube. Examples of tubulars include, but are not limited to, a drill pipe, a casing, a tubing string, a line pipe, and a transportation pipe. Tubulars can also be used to transport fluids into or out of a subterranean formation, such as oil, gas, water, liquefied methane, coolants, and heated fluids. For example, a tubular can be placed underground to transport produced hydrocarbons or water from a subterranean formation to another location.

As used herein, the term "annulus" means the space between two generally cylindrical objects, one inside the other. The objects can be concentric or eccentric. Without limitation, one of the objects can be a tubular and the other object can be an enclosed conduit. The enclosed conduit can be a wellbore or borehole or it can be another tubular. The following are some non-limiting examples illustrate some situations in which an annulus can exist. Referring to an oil, gas, or water well, in an open hole well, the space between the outside of a tubing string and the borehole of the wellbore is an annulus. In a cased hole, the space between the outside of the casing the borehole is an annulus. In addition, in a cased hole there may be an annulus between the outside cylindrical portion of a tubular such as a production tubing string and the inside cylindrical portion of the casing. An annulus can be a space through which a fluid can flow or it can be filled with a material or object that blocks fluid flow, such as a packing element. Unless otherwise clear from the context, as used herein an annulus is a space through which a fluid can flow.

As used herein, a "well fluid" broadly refers to any fluid adapted to be introduced into a well for any purpose. A well fluid can be, for example, a drilling fluid, a cement composition, a treatment fluid, or a spacer fluid. If a well fluid is to be used in a relatively small volume, for example less than about 200 barrels (32 m$^3$), it is sometimes referred to as a wash, dump, slug, or pill.

Drilling fluids, also known as drilling muds or simply "muds," are typically classified according to their base fluid (that is, the continuous phase). A water-based mud ("WBM") has solid particulate (e.g., clays, bulk density increasing agents, lost circulation materials,) suspended in an aqueous liquid as the continuous phase. The water can be brine. A brine-based drilling fluid is a water-based mud in which the aqueous component is brine. In some cases, oil may be emulsified in a water-based drilling mud. An oil-based mud ("OBM") has solid particulate suspended in oil as the continuous phase. In some cases, an aqueous phase of water or brine is emulsified in the oil. Drill Cuttings from the formation will be the additional solid particulates getting suspended in both oil-based and water based muds as the drilling process begins.

As used herein, the word "treatment" refers to any treatment for changing a condition of any portion of a wellbore or an adjacent subterranean formation; however, the word "treatment" does not necessarily imply any particular treatment purpose. A treatment usually involves introducing a well fluid for the treatment, in which case it may be referred to as a treatment fluid, into a well. As used herein, a "treatment fluid" is a fluid used in a treatment. The word "treatment" in the term "treatment fluid" does not necessarily imply any particular treatment or action by the fluid.

As used herein, the terms spacer fluid, wash fluid, and inverter fluid can be used interchangeably. A spacer fluid is a fluid used to physically separate one special-purpose fluid from another. It may be undesirable for one special-purpose fluid to mix with another used in the well, so a spacer fluid compatible with each is used between the two. A spacer fluid is usually used when changing between well fluids used in a well.

For example, a spacer fluid is used to change from a drilling fluid during drilling to cement composition during cementing operations in the well. In case of an oil-based drilling fluid, it should be kept separate from a water-based cementing fluid. In changing to the latter fluid, a chemically treated water-based spacer fluid is usually used to separate the drilling fluid from the water-based cementing fluid.

A spacer fluid specially designed to separate a special purpose oil-external fluid from a special purpose water-external fluid may be termed as an inverter fluid. Inverter fluids may be so designed that the diffused contaminated layer between both the special purpose fluids has progressive variation in properties like solids carrying capability, electrical conductivity, rheology, and chemical potential. In other words, inverter fluids may be ideally designed to be fully compatible physically and chemically with either or both of the special purpose fluids under the simulated conditions of pressure, temperature and shear. Compatibility may be warranted by rheological investigations or visual observations at all intermediate compositions. Unwanted flocculation, coagulation, or excessive thinning of the admixture compared to the original fluids is typically considered to be a signature for incompatibility.

In the context of cementing, compatibility can be determined by monitoring viscosity upon mixing. For compatibility, the viscosity of any mixture of two well fluids should be between the viscosity of either fluid. For example, the viscosity of an oil-based drilling mud may be, for example, about 100 cP. The viscosity of a spacer fluid may be, for example, about 200 cP. These two well fluids would be considered compatible if the viscosity of any mixture of the two fluids is in the range of about 100 cP to about 200 cP; but if outside this viscosity range, then a high degree of fingering, channeling, gelling, settling, separating, etc. would be likely to occur on mixing the two fluids. The proper selection of well fluids must be used for a successful cementing operation.

Volumes of spacer fluid that are consumed in channel lengths due to contamination process are not sufficient to clean wellbore surfaces or change wetting of a surface. These volumes should be considered sacrificial and the amount of pure uncontaminated spacer is estimated from surface wetting techniques.

A zone refers to an interval of rock along a wellbore that is differentiated from uphole and downhole zones based on hydrocarbon content or other features, such as permeability, composition, perforations or other fluid communication with the wellbore, faults, or fractures. A zone of a wellbore that penetrates a hydrocarbon-bearing zone that is capable of producing hydrocarbon is referred to as a "production zone." A "treatment zone" refers to an interval of rock along a wellbore into which a well fluid is directed to flow from the wellbore. As used herein, "into a treatment zone" means into and through the wellhead and, additionally, through the wellbore and into the treatment zone.

As used herein, a downhole fluid is an in-situ fluid in a well, which may be the same as a well fluid at the time it is introduced, or a well fluid mixed with another fluid downhole, or a fluid in which chemical reactions are occurring or have occurred in-situ downhole.

Generally, the greater the depth of the formation, the higher the static temperature and pressure of the formation. Initially, the static pressure equals the initial pressure in the formation before production. After production begins, the static pressure approaches the average reservoir pressure.

A "design" refers to the estimate or measure of one or more parameters planned or expected for a particular stage of a well service or associated well fluid. For example, a fluid can be designed to have components that provide a minimum viscosity for at least a specified time under expected downhole conditions. A well service may include design parameters such as fluid volume to be pumped, required pumping time for a treatment, or the shear conditions of the pumping, and contact time of a treatment fluid with a zone of interest.

The term "design temperature" refers to an estimate or measurement of the actual temperature at the downhole environment at the time of a well treatment. That is, design temperature takes into account not only the bottom hole static temperature ("BHST"), but also the effect of the temperature of the well fluid on the BHST during treatment. The design temperature is sometimes referred to as the bottom hole circulation temperature ("BHCT"). Because treatment fluids may be considerably cooler than BHST, the difference between the two temperatures can be quite large. Ultimately, if left undisturbed, a subterranean formation will return to the BHST.

Substances and Chemicals

A substance can be a pure chemical or a mixture of two or more different chemicals.

A pure chemical is a sample of matter that cannot be separated into simpler components without chemical change. A chemical element is composed of atoms with identical atomic number. A chemical compound is formed from different elements chemically combined in definite proportions by mass.

An atom or molecule is the smallest particle of a chemical that retains the chemical properties of the element or compound. A molecule is two or more chemically bound atoms with characteristic composition and structure. Making or breaking bonds in a molecule changes it to a different chemical.

An ionic compound is made of distinguishable ions, including at least one cation (a positively charged ion) and at least one anion (a negatively charged ion), held together by electrostatic forces. An ion is an atom or molecule that has acquired a charge by either gaining or losing electrons. An ion can be a single atom or molecular. An ion can be separated from an ionic compound, for example, by dissolving the ions of the compound in a polar solvent.

Physical States, Phases, and Materials

As used herein, "phase" is used to refer to a substance having a chemical composition and physical state that is distinguishable from an adjacent phase of a substance having a different chemical composition or a different physical state.

The word "material" is often used as a synonym for a single phase of a bulk scale (larger than a particle), although it can sometimes mean a bulk scale of a mixture of phases, depending on the context.

As used herein, if not other otherwise specifically stated, the physical state or phase of a substance (or mixture of substances) and other physical properties are determined at a temperature of 77° F. (25° C.) and a pressure of 1 atmosphere (Standard Laboratory Conditions) without applied shear.

Continuum Mechanics and Rheology

One of the purposes of identifying the physical state or phase of a substance and measuring viscosity or other physical characteristics of a fluid is to establish whether it is pumpable. In the context of oil and gas production, the pumpability of a fluid is with particular reference to the ranges of physical conditions that may be encountered at a wellhead and with the types and sizes of pumps available to be used for pumping fluids into a well. Another purpose is to determine what the physical state of the substance and its physical properties will be during pumping through a wellbore and under other downhole conditions in the well, including over time and changing temperatures, pressures, and shear rates.

Continuum mechanics is a branch of mechanics that deals with the analysis of the kinematics and the mechanical behavior of materials modeled as a continuous mass on a large scale rather than as distinct particles. Fluid mechanics is a branch of continuum mechanics that studies the physics of continuous materials that take the shape of their container. Rheology is the study of the flow of matter: primarily in the liquid state, but also as "soft solids" or solids under conditions in which they respond with plastic flow rather than deforming elastically in response to an applied force. It applies to substances that have a complex structure, such as fluid suspensions, gels, etc. The flow of such substances cannot be fully characterized by a single value of viscosity, which varies with temperature, pressure, and other factors. For example, ketchup can have its viscosity reduced by shaking (or other forms of mechanical agitation) but water cannot.

Particles, Particulates, Aggregates, and Fibers

As used herein, a "particle" refers to a body having a finite mass and sufficient cohesion such that it can be considered as an entity but having relatively small dimensions. A particle can be of any size ranging from molecular scale to macroscopic, depending on context.

A particle can be in any physical state. For example, a particle of a substance in a solid state can be as small as a few molecules on the scale of nanometers up to a large particle on the scale of a few millimeters, such as large grains of sand. Similarly, a particle of a substance in a liquid state can be as small as a few molecules on the scale of nanometers or a large drop on the scale of a few millimeters.

As used herein, "particulate" or "particulate material" refers to matter in the physical form of distinct particles in a solid or liquid state (which means such an association of a few atoms or molecules). A particulate is a grouping of particles based on common characteristics, including chemical composition and particle size range, particle size distribution, or median particle size. As used herein, a particulate is a grouping of particles having similar chemical composition and particle size ranges anywhere in the range of about 1 micrometer (e.g., microscopic clay or silt particles) to about 3 millimeters (e.g., large grains of sand).

As used herein, a particle can be an aggregate or a composite of different solid phases bound together.

It should be understood that the terms "particle" and "particulate," includes all known shapes of particles including substantially rounded, spherical, oblong, ellipsoid, rod-like, fiber, polyhedral (such as cubic materials), etc., and mixtures thereof. For example, the term "particulate" as used herein is intended to include solid particles having the physical shape of platelets, shavings, flakes, ribbons, rods, strips, spheroids, toroids, pellets, tablets or any other physical shape.

As used herein, a fiber is a particle or grouping of particles having an aspect ratio L/D greater than 5/1.

Dispersions

A dispersion is a system in which particles of a substance of one chemical composition and physical state are dispersed in another substance of a different chemical composition or physical state. If a substance has more than one phase, the most external phase is referred to as the continuous phase of the substance as a whole, regardless of the number of different internal phases or nested phases.

A dispersion can be classified a number of different ways, including based on the size of the dispersed particles, the uniformity or lack of uniformity of the dispersion, and, if a fluid, whether or not precipitation occurs.

Classification of Dispersions: Heterogeneous and Homogeneous

A dispersion is considered to be heterogeneous if the dispersed particles are not dissolved and are greater than about 1 nanometer in size. (For reference, the diameter of a molecule of toluene is about 1 nm).

Heterogeneous dispersions can have gas, liquid, or solid as an external phase. For example, in a case where the dispersed-phase particles are liquid in an external phase that is another liquid, this kind of heterogeneous dispersion is more particularly referred to as an emulsion. A solid dispersed phase in a continuous liquid phase is referred to as a sol, suspension, or slurry, partly depending on the size of the dispersed solid particulate.

A dispersion is considered to be homogeneous if the dispersed particles are dissolved in solution or the particles are less than about 1 nanometer in size. Even if not dissolved, a dispersion is considered to be homogeneous if the dispersed particles are less than about 1 nanometer in size.

Classification of Heterogeneous Dispersions: Suspensions and Colloids

Heterogeneous dispersions can be further classified based on the dispersed particle size.

A heterogeneous dispersion is a "suspension" where the dispersed particles are larger than about 50 micrometer. Such particles can be seen with a microscope, or if larger than about 50 micrometers (0.05 mm), with the unaided human eye. The dispersed particles of a suspension in a liquid external phase may eventually separate on standing, e.g., settle in cases where the particles have a higher density than the liquid phase. Suspensions having a liquid external phase are essentially unstable from a thermodynamic point of view; however, they can be kinetically stable over a long period depending on temperature and other conditions.

A heterogeneous dispersion is a "colloid" where the dispersed particles range up to about 50 micrometer (50,000 nanometers) in size. The dispersed particles of a colloid are so small that they settle extremely slowly, if ever. In some cases, a colloid can be considered as a homogeneous mixture. This is because the distinction between "dissolved" and "particulate" matter can be sometimes a matter of approach, which affects whether or not it is homogeneous or heterogeneous.

Classification of Homogeneous Dispersions: Solutions

A solution is a special type of homogeneous mixture. A solution is considered homogeneous: (a) because the ratio of solute to solvent is the same throughout the solution; and (b) because solute will never settle out of solution, even under powerful centrifugation, which is due to intermolecular attraction between the solvent and the solute. An aqueous solution, for example, saltwater, is a homogenous solution in which water is the solvent and salt is the solute.

One may also refer to the solvated state, in which a solute ion or molecule is complexed by solvent molecules. A chemical that is dissolved in solution is in a solvated state. The solvated state is distinct from dissolution and solubility. Dissolution is a kinetic process, and is quantified by its rate. Solubility quantifies the concentration of the solute at which there is dynamic equilibrium between the rate of dissolution and the rate of precipitation of the solute. Dissolution and solubility can be dependent on temperature and pressure, and may be dependent on other factors, such as salinity or pH of an aqueous phase.

Solubility Terms

A substance is considered to be "soluble" in a liquid if at least 10 grams of the substance can be dissolved in one liter of the liquid when tested at 77° F. and 1 atmosphere pressure for 2 hours and considered to be "insoluble" if less soluble than this.

As will be appreciated by a person of skill in the art, the hydratability, dispersibility, or solubility of a substance in water can be dependent on the salinity, pH, or other substances in the water. Accordingly, the salinity, pH, and additive selection of the water can be modified to facilitate the hydratability, dispersibility, or solubility of a substance in aqueous solution. To the extent not specified, the hydratability, dispersibility, or solubility of a substance in water is determined in deionized water, at neutral pH, and without any other additives.

Dielectric constants are not the only measures of polarity but generally, dielectric constant of the material provides a rough measure of the material's polarity. As used herein, the term "polar" means having a dielectric constant greater than 15. The term "relatively polar" means having a dielectric constant greater than about 5 and less than about 15 "Nonpolar" means having a dielectric constant less than 5.

Fluids

A fluid can be a single phase or a dispersion. In general, a fluid is an amorphous substance that is or has a continuous phase of particles that are smaller than about 1 micrometer that tends to flow and to conform to the outline of its container.

Examples of fluids are gases and liquids. A gas (in the sense of a physical state) refers to an amorphous substance that has a high tendency to disperse (at the molecular level) and a relatively high compressibility. A liquid refers to an amorphous substance that has little tendency to disperse (at the molecular level) and relatively high incompressibility. The tendency to disperse is related to Intermolecular Forces (also known as van der Waal's Forces). (A continuous mass of a particulate, e.g., a powder or sand, can tend to flow as a fluid depending on many factors such as particle size distribution, particle shape distribution, the proportion and nature of any wetting liquid or other surface coating on the particles, and many other variables. Nevertheless, as used herein, a fluid does not refer to a continuous mass of particulate because the sizes of the solid particles of a mass of a particulate are too large to be appreciably affected by the range of Intermolecular Forces.)

As used herein, a fluid is a substance that behaves as a fluid under Standard Laboratory Conditions, that is, at 77° F. (25° C.) temperature and 1 atmosphere pressure, and at the higher temperatures and pressures usually occurring in subterranean formations without applied shear.

Every fluid inherently has at least a continuous phase. A fluid can have more than one phase. The continuous phase of a well fluid is a liquid under Standard Laboratory Conditions. For example, a well fluid can in the form of be a suspension (solid particles dispersed in a liquid phase), an emulsion (liquid particles dispersed in another liquid phase), or a foam (a gas phase dispersed in liquid phase).

As used herein, a water-based fluid means that water or an aqueous solution is the dominant material of the continuous phase, that is, greater than 50% by weight, of the continuous phase of the substance.

In contrast, "oil-based" means that oil is the dominant material by weight of the continuous phase of the substance. In this context, the oil of an oil-based fluid can be any oil. In general, an oil is any substance that is liquid Standard Laboratory Conditions, is hydrophobic, and soluble in organic solvents. Oils have a high carbon and hydrogen content and are relatively non-polar substances, for example, having a dielectric constant of 1.5 to 5. This general definition includes classes such as petrochemical oils, vegetable oils, and many organic solvents. All oils can be traced back to organic sources.

Apparent Viscosity of a Fluid

Viscosity is a measure of the resistance of a fluid to flow. In everyday terms, viscosity is "thickness" or "internal friction." Thus, pure water is "thin," having a relatively low viscosity whereas honey is "thick," having a relatively higher viscosity. Put simply, the less viscous the fluid is, the greater its ease of movement (fluidity). More precisely, viscosity is defined as the ratio of shear stress to shear rate.

A fluid moving along solid boundary will incur a shear stress on that boundary. The no-slip condition dictates that the speed of the fluid at the boundary (relative to the boundary) is zero, but at some distance from the boundary, the flow speed must equal that of the fluid. The region between these two points is named the boundary layer.

A Newtonian fluid (named after Isaac Newton) is a fluid for which stress versus strain rate curve is linear and passes through the origin. The constant of proportionality is known as the viscosity. Examples of Newtonian fluids include water and most gases. Newton's law of viscosity is an approximation that holds for some substances but not others.

Non-Newtonian fluids exhibit a more complicated relationship between shear stress and velocity gradient (i.e., shear rate) than simple linearity. Thus, there exist a number of forms of non-Newtonian fluids. Shear thickening fluids have an apparent viscosity that increases with increasing the rate of shear. Shear thinning fluids have a viscosity that decreases with increasing rate of shear. Thixotropic fluids become less viscous over time at a constant shear rate. Rheopectic fluids become more viscous over time at a constant sear rate. A Bingham plastic is a material that behaves as a solid at low stresses but flows as a viscous fluid at high stresses.

Most well fluids are non-Newtonian fluids. Accordingly, the apparent viscosity of a fluid applies only under a particular set of conditions including shear stress versus shear rate, which must be specified or understood from the context. As used herein, a reference to viscosity is actually a reference to an apparent viscosity. Apparent viscosity is commonly expressed in units of centipoise ("cP").

Like other physical properties, the viscosity of a Newtonian fluid or the apparent viscosity of a non-Newtonian fluid may be highly dependent on the physical conditions, primarily temperature and pressure.

Viscosity Measurements

There are numerous ways of measuring and modeling viscous properties, and new developments continue to be made. The methods depend on the type of fluid for which viscosity is being measured. A typical method for quality assurance or quality control (QA/QC) purposes uses a Couette device, such as a Fann Model 35 or 50 viscometer or a Chandler 5550 HPHT viscometer, that measures viscosity as a function of time, temperature, and shear rate. The viscosity-measuring instrument can be calibrated, for example, by using standard viscosity silicone oils or other standard viscosity fluids.

Unless otherwise specified, the apparent viscosity of a fluid (excluding any suspended solid particulate larger than silt) is measured with a Fann Model 35 type viscometer using an R1 rotor, B1 bob, and F1 torsion spring at a shear rate of 40 1/s, and at a temperature of 77° F. (25° C.) and a pressure of 1 atmosphere. For reference, the viscosity of pure water is about 1 cP.

A substance is considered to be a fluid if it has an apparent viscosity less than 5,000 cP (independent of any gel characteristic).

Cement Compositions

As used herein, "cement" refers to an inorganic cement (as opposed to organic cement and adhesives) that when mixed with water will begin to set and harden.

As used herein, a "cement composition" is a material including at least cement. A cement composition can also include additives. A cement composition can include water or be mixed with water.

A cement can be characterized as non-hydraulic or hydraulic.

Non-hydraulic cements (e.g., gypsum plaster, Sorel cements) must be kept dry in order to retain their strength.

Hydraulic cements (e.g., Portland cement) harden because of hydration, chemical reactions that occur independently of the mixture's water content; they can harden even underwater or when constantly exposed to wet weather. The chemical reaction that results when the dry cement powder is mixed with water produces hydrates that have extremely low solubility in water. The cement composition sets by a hydration process, and it passes through a gel phase to solid phase.

During well completion, it is common to introduce a cement composition into an annulus in the wellbore. For example, in a cased hole, the cement composition is placed into and allowed to set in the annulus between the wellbore and the casing in order to stabilize and secure the casing in the wellbore. After setting, the set cement composition should have a low permeability. Consequently, oil or gas can be produced in a controlled manner by directing the flow of oil or gas through the casing and into the wellhead. Cement compositions can also be used, for example, in well-plugging operations or gravel-packing operations.

Emulsions

An emulsion is a fluid including a dispersion of immiscible liquid particles in an external liquid phase. In addition, the proportion of the external and internal phases is above the solubility of either in the other. A chemical can be included to reduce the interfacial tension between the two immiscible liquids to help with stability against coalescing of the internal liquid phase, in which case the chemical may be referred to as a surfactant, an emulsifier, or emulsifying agent.

An emulsion can be an oil-in-water (o/w) type or water-in-oil (w/o) type. A water-in-oil emulsion is sometimes referred to as an invert emulsion. In the context of an emulsion, a "water phase" refers to a phase of water or an aqueous solution and an "oil phase" refers to a phase of any non-polar organic liquid that is immiscible with water, such as petroleum, kerosene, or synthetic oil.

A stable emulsion is an emulsion that will not cream, flocculate, or coalesce under certain conditions, including time and temperature. As used herein, the term "cream" means at least some of the droplets of a dispersed phase converge towards the surface or bottom of the emulsion (depending on the relative densities of the liquids making up the continuous and dispersed phases). The converged droplets maintain a discrete droplet form. As used herein, the term "flocculate" means at least some of the droplets of a dispersed phase combine to form small aggregates in the emulsion. As used herein, the term "coalesce" means at least some of the droplets of a dispersed phase combine to form larger drops in the emulsion.

Surfactant or Emulsifier

As used herein, a surfactant or emulsifier refers to a substance that helps prevent the droplets of the dispersed phase of an emulsion from flocculating or coalescing in the emulsion. The efficacy of a surfactant is known to be measured using techniques like penetrative displacement and immersion wetting and using parameters like spreading coefficient and partition coefficient.

Surfactants contain both hydrophobic and hydrophilic groups, that is, a molecule that contains both oil soluble as well as water-soluble components. These molecules diffuse in water and adsorb at interfaces between oil and water. The insoluble hydrophobic group extends out from the bulk water phase towards the oil phase while the water-soluble group remains in the water phase. Alignment of these molecules modifies the surface properties of the oil-water interface.

A surfactant or emulsifier can be or include a cationic, a zwitterionic, or a nonionic emulsifier. A surfactant package can include one or more different chemical surfactants.

A surfactant package may be included in a fluid that is being deployed for a clean-out operation. The surfactant package may include one or more water-soluble surfactants, one or more oil soluble surfactants, and one or more emulsifiers.

General Measurement Terms

Unless otherwise specified or unless the context otherwise clearly requires, any ratio or percentage means by weight.

Unless otherwise specified or unless the context otherwise clearly requires, the phrase "by weight of the water" means the weight of the water of the continuous phase of the fluid without the weight of any viscosity-increasing agent, dissolved salt, suspended particulate, or other materials or additives that may be present in the water.

If there is any difference between U.S. or Imperial units, U.S. units are intended.

The barrel is the unit of measure used in the US oil industry, wherein one barrel equals 42 U.S. gallons. Standards bodies such as the American Petroleum Institute (API) have adopted the convention that if oil is measured in oil barrels, it will be at 14.696 psi and 60° F., whereas if it is measured in cubic meters, it will be at 101.325 kPa and 15° C. (or in some cases 20° C.). The pressures are the same but the temperatures are different −60° F. is 15.56° C., 15° C. is 59° F., and 20° C. is 68° F. However, if all that is needed is to convert a volume in barrels to a volume in cubic meters without compensating for temperature differences, then 1 bbl equals 0.159 m³.

A Method According to the Invention

According to an embodiment, a method is provided including the steps of:
(A) obtaining or providing an apparatus comprising:
  (i) a container forming a chamber;
  (ii) a first surface exposed to or in the chamber, wherein the first surface is of:
    (a) a first electrode, or
    (b) a first dielectric solid material in contact with the first electrode;
  (iii) a second surface exposed to or in the chamber, wherein the second surface is of:
    (a) a second electrode, or
    (b) a second dielectric solid material in contact with the second electrode;
  wherein the first surface is electrically insulated from the second surface;
(B) wetting at least the first surface with a first liquid phase of a first bulk fluid;
(C) after the step of wetting, introducing a bulk fluid into the chamber, wherein the bulk fluid comprises a second liquid phase, and wherein the second liquid phase is immiscible with the first liquid phase;
(D) applying a shear between the second bulk fluid in the chamber and at least the first surface; and
(E) making an electrical impedance spectroscopy measurement between the first and second electrode.

According to another preferred embodiment of this method, it additionally includes the steps of: before the step of applying the shear, making a first electrical impedance spectroscopy measurement between the first and second electrode; during or after the step of applying the shear, making a second electrical impedance spectroscopy measurement between the first and second electrode; comparing the first electrical impedance spectroscopy measurement to the second electrical impedance spectroscopy measurement; and based on the step of comparing, inferring any changes in the wetting of the first surface. Preferably, the step of inferring comprises assuming an equivalent electrical circuit model to match experimental impedance changes using non-linear regression techniques.

According to yet another embodiment of the invention, a method is provided including the steps of: (A) positioning a first electrode and a second electrode in an annulus between a metallic tubular and the borehole of a wellbore in a well; (B) pumping a fluid through though the annulus and between the first electrode and the second electrode; and (C) at least once during or after the step of pumping, making an electrical impedance spectroscopy measurement between the first and second electrode. It should be understood that the first and second electrodes are electrically insulated from the tubular and the flow path for electrical current is through the fluid in the annulus.

According to a presently most preferred embodiment, the step of taking an electrical impedance spectroscopy measurement includes: operatively connecting an alternating electrical potential source between the first and second electrodes; while operatively connected to the first and second electrodes, varying the electrical potential or the frequency of the alternating electrical potential source; and while varying the electrical potential or the frequency of the alternating electrical potential source, measuring electrical impedance between the first electrode and second electrode to obtain an electrical impedance spectroscopy measurement.

An Apparatus According to the Invention

According to another embodiment of the invention, an apparatus is provided including:
(A) a container forming a chamber;
(B) a first surface exposed to or in the chamber, wherein the first surface is of:
  (i) a first electrode, or
  (ii) a first dielectric solid material in contact with the first electrode;
(C) a second surface exposed to or in the chamber, wherein the second surface is of:
  (i) a second electrode, or
  (ii) a second dielectric solid material in contact with the second electrode,
  wherein the first surface is electrically insulated from the second surface;
(D) a first liquid phase wetted on at least the first surface;
(E) a bulk fluid in the chamber, wherein the bulk fluid comprises a second liquid phase, and wherein the second liquid phase is immiscible with the first liquid phase;
(F) a means for controlling the shear rate between the bulk fluid in the chamber and at least the first surface;
(G) an alternating electrical potential source operatively connected between the first and second electrodes;
(H) means for controlling the electrical potential or the frequency of the alternating electrical potential source; and
(I) means for measuring changes in electrical impedance between the first electrode and second electrode;
whereby electrical impedance spectroscopy measurements can be made between the first electrode and the second electrode before, during, or after controlling the shear rate.

According to a preferred embodiment of this apparatus, the first surface is curved.

Applications of the Invention

Various fluids and surfactants are used in wells that may change the wettability or wetting of downhole solid surfaces.

This invention relates to techniques that can be used to test, under simulated downhole conditions, the surface wetting, film cleaning capability, or other effect of a fluid on various surfaces. This can be used, for example, to test and quantify the water-wetting efficiency of a fluid that is to be pumped into a well. It can be used, for example, to test, under simulated conditions, the wetted status of a downhole surface after exposure to a downhole fluid.

According to an embodiment of the invention, a technique of electrical impedance spectroscopy can be used to measure the percentage area of coverage by water or, conversely, area of coverage by oil on a surface under conditions that simulate downhole conditions in a well. The percentage of surface wetting with water or oil can be measured using this method, non-invasively and without the use of visual inspection, or imaging, or goniometry methods that have been known to be associated with error and non-repeatability.

In an embodiment, the invention can be useful in determining the wettability or wetting of surfaces in wells, including the surfaces of tubulars or a subterranean formation. This information can be used in the design of various well services and well fluids.

In an embodiment, the invention can be used for designing well fluids such as drilling fluids, spacer fluids, and cement compositions, or for designing the conditions of introducing such well fluids into a well.

In yet another embodiment, the invention can be used as part of a job for completing or stimulating a zone in a well.

Applications to Cementing

An example of an application of the invention is to cementing. Hydraulic cement does not bond to oil-wet surfaces. Surface wettability with water is of primary importance to achieve good cement bonding to a metallic pipe. It is also important to achieve good cement bonding to adjacent rock surfaces of a subterranean formation. The quality of a cement bond to a surface can be expected to be very good if 100% water wetting of the surface is achieved.

Calcium, aluminum, and silicon ions of the cement slurry couple by electrical charges across an interface with ferrous and ferric hydroxide ions on the surface of the steel. Iron atoms couple with the unbalanced oxygen atoms in the cement paste. This bonding between the iron atoms and hydroxyl groups in the cement is often described by a hydrogen-bonding coupling with a pair of electrons that are held in the outer fourth orbit of the iron atom.

The cement-steel interface is weaker than the bulk of the cement itself. Increased chances of loss of zonal isolation occur if the complete surface area is not bonded to the cement. Any reduction in the percentage of water-wet area increases the non-bonded area, thereby reducing the shear bond strength of the cement sheath and its competence to isolate zones.

Researchers in the area of cement and concrete have previously reported that the interface between concrete and steel surfaces is influenced by bleeding and entrapment of water against the surface of the steel and the less-compact arrangement of the small cement particles that form a layer adjacent to the metal surface. The diameter of the cement particles is typically in the range of about 10 to about 50 micrometer. The weakest zone at the cement-steel interface during the setting process is associated with a porous paste-like zone. This porous paste gradually hardens in the course of the cement slurry setting process and is associated with the formation of ferrous and ferric hydroxides that are not tightly bonded to the silicate gel in the paste.

A water-wetted metal surface allows for the formation of a stronger and more completely bonded cement-steel interface. Similarly, a water-wetted rock surface of a subterranean formation allows for the formation of a stronger and more completely bonded cement-rock interface. Accordingly, in a cementing operation, it is important to try to change an oil-wetted surface to a water-wetted surface prior to placing the cement composition in the portion of the wellbore to be cemented.

FIGS. 1a, 1b, and 1c are illustrations of a sequence of fluid displacement in a wellbore during a cementing operation. A spacer fluid 30 is illustrated being pumped into a wellbore of a well penetrating a formation 10 and down through a casing 12 (which has not yet been cemented) and then out the lower end of the casing and up through the annulus 14 between the outside of the casing 12 and the borehole of the wellbore. FIG. 1a illustrates a drilling mud 20 initially the annulus 14 of the wellbore around the casing 12. FIG. 1b illustrates a spacer fluid 30 being pumped through the casing to displace the drilling mud 20 from the annulus 14. FIG. 1c illustrates a cement composition 40 (sometimes referred to as a cement slurry) being pumped through the casing 12 to displace the spacer fluid 30 and placed in the annulus 14 for cementing the casing 12 in the wellbore penetrating the formation 10. To seal the annulus 14 with cement requires good cement bonding between both the outer wall of the casing 12 and the rock of the subterranean formation 10 of the borehole.

Figure 2:
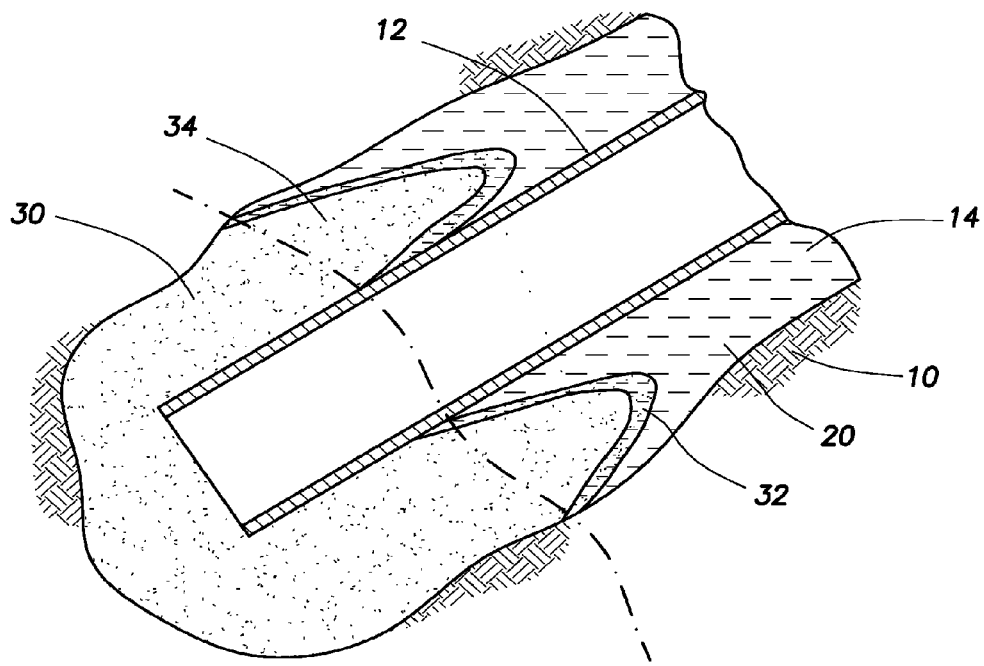
FIG. 2 is an illustration modeling fluid intermixing between a prior drilling mud in a wellbore and a spacer fluid as the spacer fluid displaces the prior well fluid, which is similar to the stage illustrated in FIG. 1b.

FIG. 2 is an illustration modeling of fluid intermixing between a prior well fluid, such as a drilling mud 20, in a wellbore penetrating a subterranean formation 10 and a spacer fluid 30 as the spacer fluid displaces the prior drilling mud 20, which is similar to the stage illustrated in FIG. 1b. In FIG. 2, the spacer fluid 30 is illustrated being pumped into the well and down through a casing 12 (which has not yet been cemented) and then out the lower end of the casing and up through the annulus 14 between the outside of the casing and the borehole of the wellbore penetrating the subterranean formation 10. As the spacer fluid displaces the prior fluid in the wellbore, there is a diffused layer 32 of mixing and channeling between the prior fluid and the spacer fluid. The diffused layer 32 includes varying mixtures of the prior fluid in the well and spacer fluid. The diffused layer 32 is sometimes referred to as contaminated spacer fluid. The spacer fluid 30 being pumped behind the diffused layer is sometimes referred to as pure or uncontaminated spacer fluid.

Figure 3:
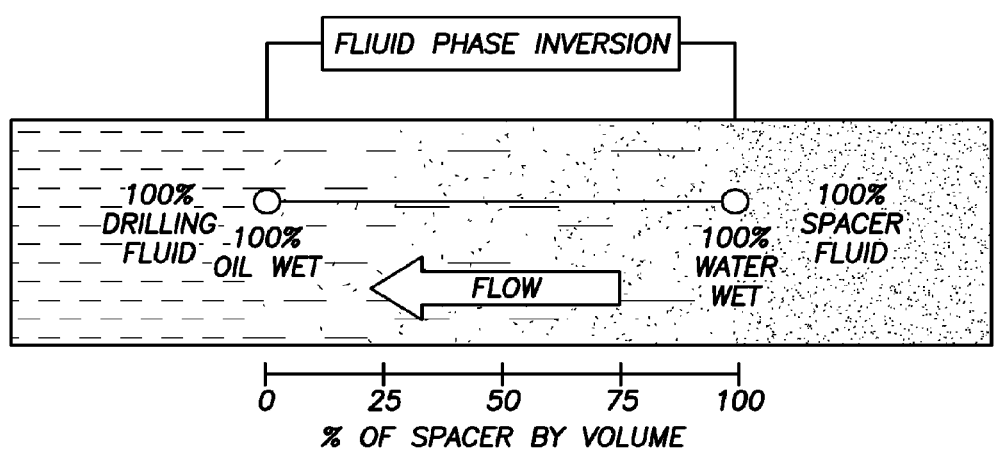
FIG. 3 is a graphical representation of a diffused layer between an oil-based drilling mud and a water-based spacer fluid, wherein at some degree of mixing and depending on the particular compositions of the oil-based and water-based fluids, the continuous phase of the fluid in the zone of the well inverts from oil-based to water-based.

FIG. 3 is a graphical representation of a diffused layer between an oil-based drilling mud and a water-based spacer fluid, wherein at some degree of mixing and depending on the particular compositions of the oil-based and water-based fluids, the continuous phase of the fluid in the zone of the well inverts from oil-based to water-based.

A method according to the invention can be used to test the effectiveness of a water-based spacer fluid for removing an oil-based drilling fluid and rendering downhole surfaces water wet prior to cement slurry placement. This method can be used to optimize the dosage of costly surfactant packages, annular pump rates, and contact times in spacer fluids at downhole conditions. In addition, the method can be extended to perform quality check on cement to pipe bonding after cement setting.

Fundamental Electrical Concepts

A conductor is a substance that contains movable electric charges. In metallic conductors such as copper or aluminum, the movable charged particles are electrons (see electrical conduction). Positive charges may also be mobile, such as the cationic electrolyte(s) of a battery, or the mobile protons of the proton conductor of a fuel cell. In general, the term wire refers to an elongated conductor.

An insulator is a non-conducting substance with few mobile charges and which support only insignificant electric currents.

The electrical resistance of an electrical element is the opposition to the passage of an electric current through that element; the inverse quantity is electrical conductance, the ease at which an electric current passes. The SI unit of electrical resistance is the ohm ($\Omega$), while electrical conductance is measured in siemens (S).

A substance of uniform cross section has a resistance proportional to its resistivity and length and inversely proportional to its cross-sectional area. All substances show some resistance, except for superconductors, which have a resistance of zero. The resistance (R) of an object is defined as the ratio of voltage across it to current through it, while the conductance (G) is the inverse.

Permittivity is a measure of the ability of a material to be polarized by an electric field. The dielectric constant of a material is the ratio of its permittivity to the permittivity of vacuum. The dielectric constant is therefore also known as the relative permittivity of the material. More particularly, in electromagnetism, absolute permittivity is the measure of the resistance that is encountered when forming an electric field in a medium. In other words, permittivity is a measure of how an electric field affects, and is affected by, a dielectric medium. The permittivity of a medium describes how much electric field (more correctly, flux) is "generated" per unit charge in that medium. Less electric flux exists in a medium with a high permittivity (per unit charge) because of polarization effects. Permittivity is directly related to electric susceptibility, which is a measure of how easily a dielectric polarizes in response to an electric field. Thus, permittivity relates to a material's ability to transmit (or "permit") an electric field.) In SI units, permittivity $\in$ is measured in farads per meter (F/m); electric susceptibility $\chi$ is dimensionless.

The continuous phase of a fluid characterizes the relative permittivity of the fluid as a whole.

Electrical Double Layer and Capacitance

Without being limited by any theory, it is postulated that the production of an electrical double layer ("EDL") occurs when a charged surface comes into contact with a polar or ionized liquid.

An electrical double layer is a structure that is formed on the surface of a charged object when it is placed in contact with a liquid. The electrical double layer is a structure that describes the variation of electric potential near a charged surface in contact with a liquid.

Figure 4:
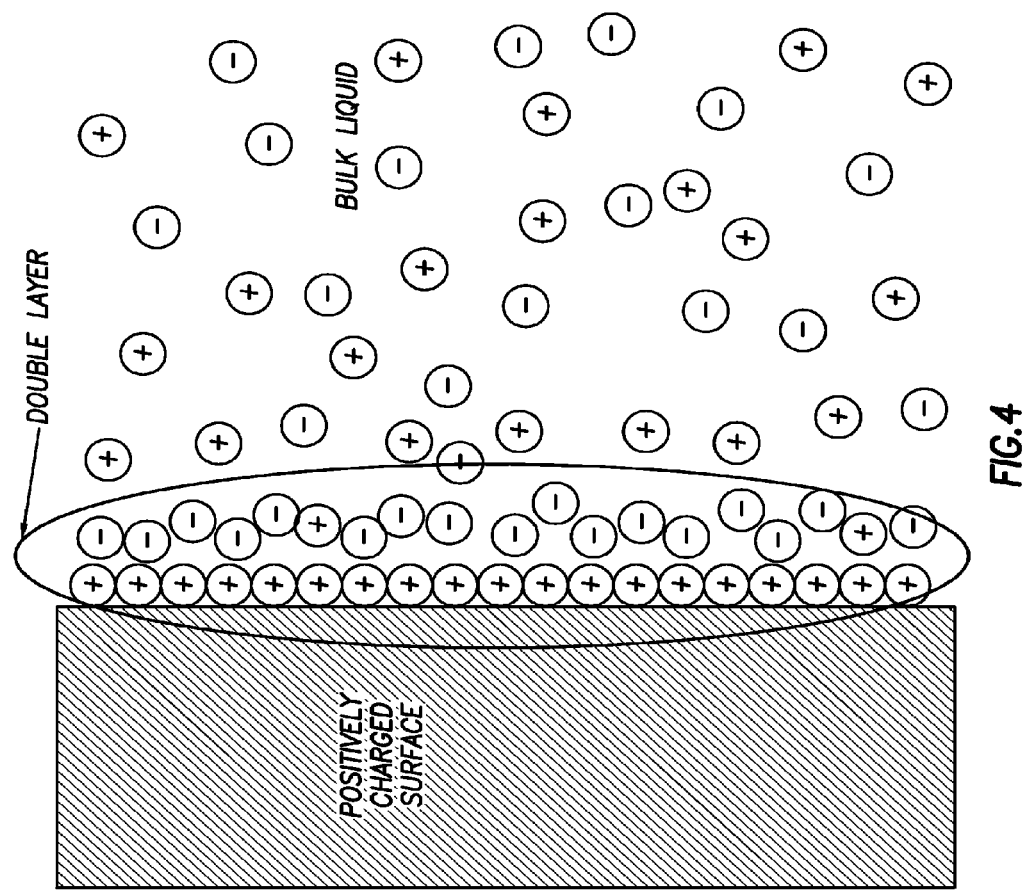
FIG. 4 illustrates the formation of an electrical double layer at the interface between a positively charged surface and a bulk liquid including electrolyte ions, without any intervening film of an oleaginous liquid phase on the positively charged surface.

The surface charge on the object creates an electrostatic field that then affects the ions in the bulk of the liquid. This electrostatic field, in combination with the thermal motion of the ions, creates a counter charge, and thus screens the electric surface charge. The net electric charge in this screening, diffuse layer is equal in magnitude to the net surface charge, but has the opposite polarity. As a result, the complete structure is electrically neutral. Some of the counter-ions may specifically adsorb near the surface and build an inner sub-layer, or so-called Stern layer. The Stern Layer is typically of the angstrom range because of the extreme proximity of the opposite charged atoms co-existing in line. The outer part of the screening layer is usually called the diffuse layer. An electrical double layer on a positively charged surface is illustrated in FIG. 4.

Figure 5:
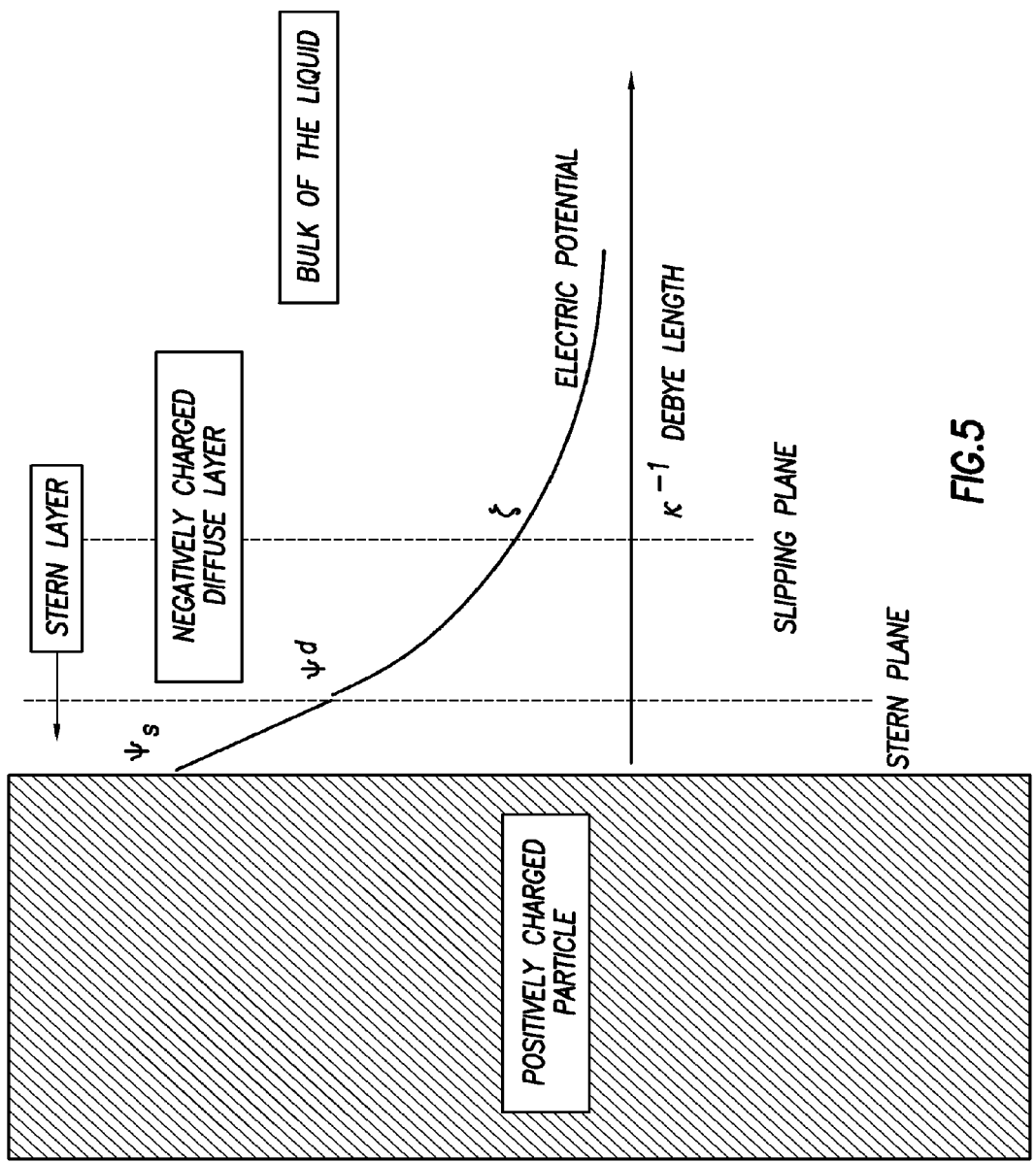
FIG. 5 is a graphical illustration of electric potential distribution of an electrical double layer as a function of the dielectric dipole moment (i.e., Debye length) of the molecules of a liquid phase, including showing the region of the slipping plane.

The diffuse layer, or at least part of it, can move under the influence of tangential stress. A slipping plane separates mobile fluid from fluid that remains attached to the surface. FIG. 5 is an illustration of electric potential distribution of an electrical double layer based on the dielectric dipole moment (i.e., Debye length) of the molecules of the liquid medium, including showing the region of the slipping plane.

An electrical double layer is often characterized by a parameter called the electrical double layer capacitance ("EDLC"). Capacitance is a function of the dielectric constant of the liquid medium present in between the charged particles in the liquid medium. Thus, the charge distribution on a charged surface is different for polar fluids (such as water-based well fluids, including aqueous spacer fluids and cementing slurries) and non-polar fluids (such as diesel, ester, or the other base oils used in oil-based drilling fluids). For the purpose of illustration, if the dielectric constant of non-polar fluids is assumed to be 20 times less than that of water. Therefore, a 20-fold increase in the capacitance can be expected in a linear variation from 100% oil wet to 100% water wet if the double layers were modeled as ideal capacitors in parallel, keeping the electrolyte constant. This difference in charge distribution patterns affects the value of double layer capacitance. Increasing percentage of surface coverage with water will thereby lead to an increase in double layer capacitance. Typically, on a conducting bare metal immersed in an electrolyte, approximately, 10 to 50 microfarad of capacitance appears on every square centimeter on the electrode. A conducting bare metal immersed in an oil-based fluid would have a much lower electrical double layer capacitance.

Electrical Impedance Spectroscopy to Test Wetting in a Complex System

Well fluids and downhole surface conditions are complex systems. In dealing with particle-laden well fluids on irregular and rough surfaces, the concept of ideal capacitor may turn out to be insufficient. Temperature, ionic concentration, types of ions, oxide layers, adsorptive species, and surface roughness influence electrical double layer capacitance. According to the invention, these are modeled as capacitors that are leaky and that have non-uniform current distribution. In addition, when a surface is polarized, it can cause current to flow through electrical interactions that are induced to occur at or near the surface. These effects can be modeled using parameters known as polarization resistance and charge transfer resistance. Electrical interactions accompanied by mass transfer are modeled using a parameter known as Warburg Impedance.

According to the invention, a combination of resistors and capacitors is used to model the impedance offered by a system. The impedance offered by the system is physically measured and subsequent mathematical modeling is carried out to calculate the values of the resistances and capacitances of the individual electrical elements. These values will be an indication of the completeness of water wetting on the surface.

An electrical circuit is completed in order to measure the impedance of the system. This can be done by building an electrical system with an oil-field well fluid.

In general, an AC circuit is used to measure impedance at a perturbation voltage and various frequencies.

Electrical properties that influence charge conductance or accumulation associated with the surfaces can be additionally modeled with this technique to study or simulate changes in the wetting on a surface in a well.

Figure 6A:
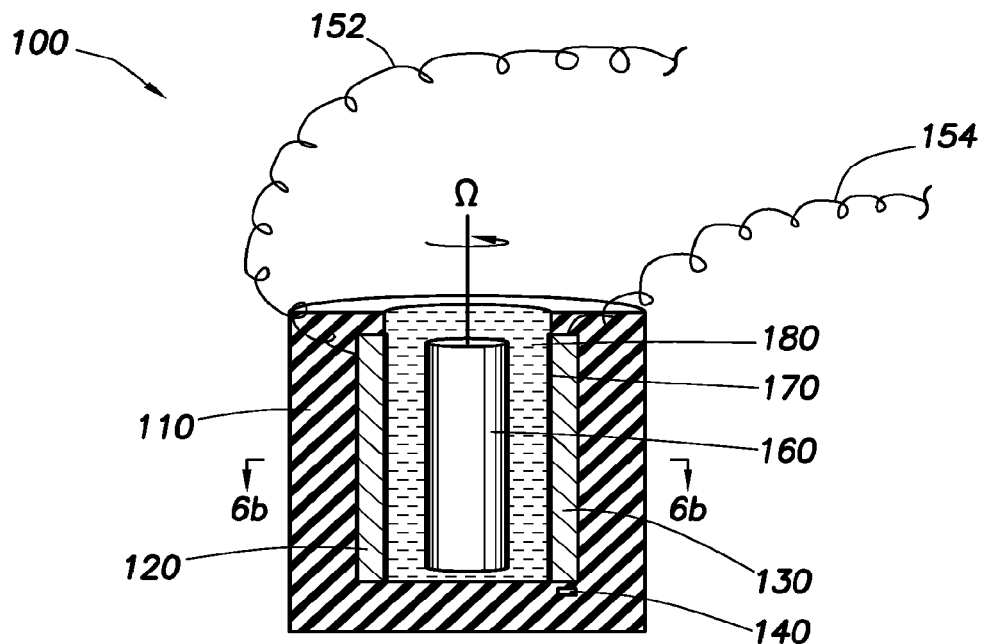
FIG. 6a is a vertical cross-sectional view of an electrical apparatus for measuring the change in surface wetting on a metal surface, which can be selected, for example, to simulate a metal surface in a well. The electrical circuit for measuring electrical impedance between the electrodes of the apparatus is not shown in detail.
Figure 6B:
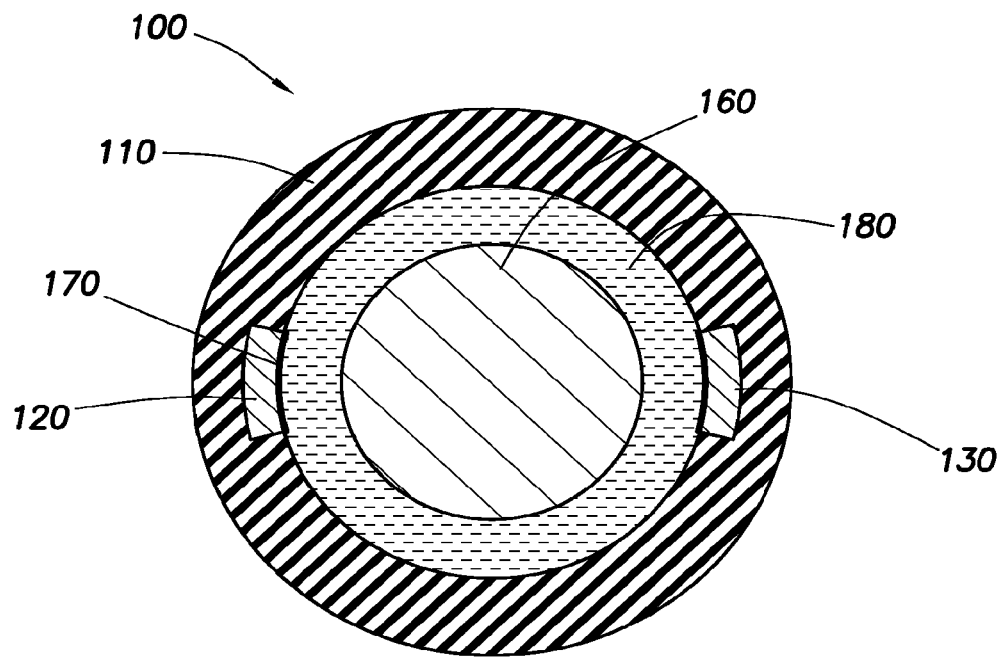
FIG. 6b is a top view of the apparatus in FIG. 6a, illustrating the insulated separation of the electrodes in the container wall of the apparatus. This type of apparatus can measure the change in surface wetting on an electrode surface from a first liquid phase to a second liquid phase as a second bulk fluid including the second liquid phase is sheared in the container of the apparatus at a controlled rate for a controlled contact time. The electrode surfaces can simulate the metallic body of a tubular. The first liquid phase can simulate a prior oleaginous film formed on the surface. The second bulk fluid can and conditions of shear and time can simulate the displacement of the oleaginous film by a spacer fluid.

According to an embodiment for simulating downhole conditions on a metallic surface, an electrical system 100 is schematically represented, in FIG. 6a and FIG. 6b. As shown in FIG. 6a, the electrical system 100 includes: an electrically insulating electrode holder or container 110, a first electrode 120; a second electrode 130, an optional reference electrode 140, a motor (not shown) for providing rotational speed Ω to a structure 160 for shearing a fluid in the container 110, wires 152 and 154 operatively connected between the first electrode 120 and the second electrode 130, respectively, to an EIS measuring device (not shown in this figure).

This system 100 is adapted for simulating and measuring the formation or removal of any wetting or coating or film 170 on the surfaces the electrodes 120 or 130 in the presence of a test fluid 180. The changes can be measured under shearing conditions applied to the test fluid 180 in the system 100. The composition of the test fluid 180 can be kept constant during a testing procedure or it can be changed continuously or intermittently by dosing another test fluid that displaces the original fluid under controlled hydrodynamic conditions. In general, the system and applied voltage is adapted such that the electrical circuit is directed across the electrodes 120 and 130 through the test fluid 180. FIG. 6b is a top view of FIG. 6a.

One or both the electrodes 120 and 130 can be used to simulate a downhole metallic material, such as a steal tubular, the test conditions of shear, and optionally temperature and pressure can be adapted to simulate downhole conditions adjacent a downhole metallic material, and the test fluid can be used to simulate a well fluid in a wellbore. In general, the system 100 can be used, as described herein, to measure any changes in any surface wetting or film 170 on the test electrodes under such simulated test conditions and with such test fluids.

The system 100 can be used to determine the removal of a film or coating on an metallic electrode surface that is needed to be removed under the effect of shear, pressure, temperature, and time conditions as may be used in the wellbore. Here, the coating can be deliberately created by applying a coating manually or can be automatically created during the process of shearing the fluid which is responsible for applying the coating in the setup. In this case, the contents and ingredients of the coating will be present in the first fluid. The second fluid will be used to remove the coating.

In one type of test procedure, for example, the second bulk fluid is poured into the container of the apparatus in the event where the film of a first liquid phase is first manually created.

In another type of procedure, for example, the coating or film is created by a first bulk fluid on the surfaces under the effect of pressure, temperature, and shear, and time. The second bulk fluid displaces the first bulk fluid, preferably under simulated well conditions of pressure, temperature, shear, and time. Any removing or cleaning the prior film on the surface under the controlled hydrodynamic conditions can be objectively measured with electrical impedance spectroscopy according to the invention.

Figure 7A:
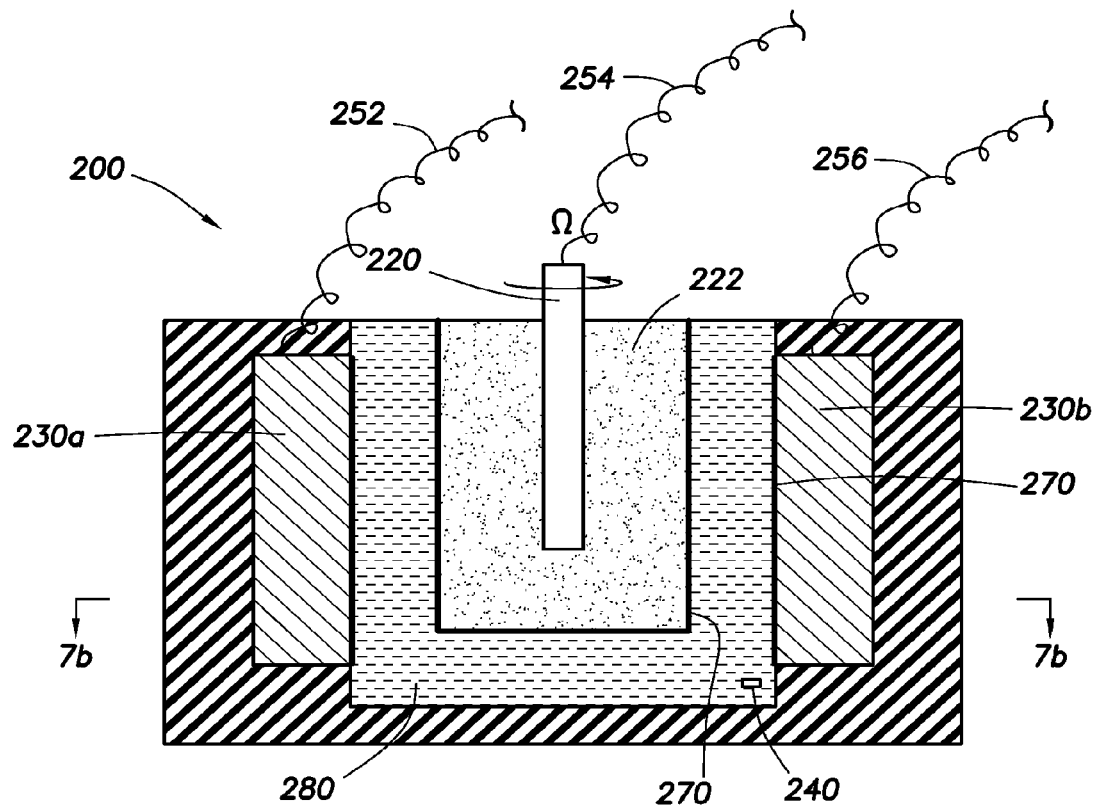
FIG. 7a is a vertical cross-sectional view of an electrical apparatus for measuring the change in surface wetting on a dielectric solid surface, which can be selected, for example, to simulate a rock surface of a subterranean formation. The electrical circuit for measuring electrical impedance between the electrodes of the apparatus is not shown in detail.
Figure 7B:
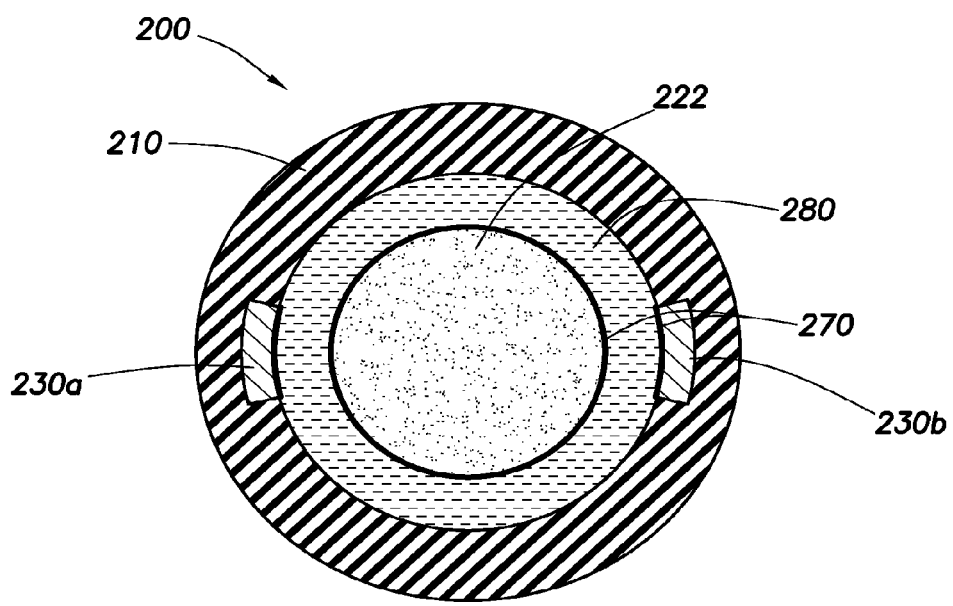
FIG. 7b is a top view of the apparatus in FIG. 7a, illustrating the insulated separation of the dielectric surfaces in the container wall of the apparatus. It should be understood, of course, that the dielectric constant of the insulating material of the container should be lower than that of any liquid phases being tested for wetting on the testing surface. Similarly, it should be understood, of course, that the dielectric constant of the insulating material of the container should be lower than that of the material of the testing surface. A first electrode is placed in electrical contact with the dielectric solid to be tested. This type of apparatus can measure the change in surface wetting on a tested dielectric surface from a first liquid phase to a second liquid phase as a second bulk fluid including the second liquid phase is sheared in the container of the apparatus at a controlled rate for a controlled contact time. The dielectric solid surfaces can be selected to simulate the rock of a subterranean formation in a well. The first liquid phase can simulate a prior oleaginous film formed on the surface of the rock. The second bulk fluid can and conditions of shear and time can simulate the displacement of the oleaginous film by a spacer fluid.

According to an embodiment for simulating downhole conditions on a rock surface, an electrical system 200 is schematically represented, in FIG. 7a and FIG. 7b. FIG. 7a is a vertical cross-sectional view of an electrical apparatus for measuring the change in surface wetting on a dielectric solid surface, which can be selected, for example, to simulate a rock surface of a subterranean formation. The electrical circuit for measuring electrical impedance between the electrodes of the apparatus is not shown in detail.

As shown in FIG. 7a, the electrical system 200 includes: an insulating electrode holder or container 210, a first electrode 220, which is centered in concentrically located formation material 222; second electrodes 230a and 230b, which can be the same as each other; an optional reference electrode 240, a motor (not shown) for providing rotational speed Ω to a structure 260 for shearing a fluid in the container 210, wires 252 and 254 operatively connected between the first electrode 220 and the second electrodes 230a and 230b to an EIS measuring device (not shown in this figure). It should be understood that two of the second electrodes 230a and 230b are not required, but rather, one of the second electrodes would suffice, if desired.

This system 200 is adapted for simulating and measuring the formation or removal of any wetting or coating or film 270 on the surfaces of the formation material 222 in the presence of a test fluid 280. The changes can be measured under shearing conditions applied to the test fluid 280 in the system 200. The composition of the test fluid 280 can be kept constant during a testing procedure or it can be changed continuously or intermittently by dosing another test fluid that displaces the original fluid under controlled hydrodynamic conditions. In general, the system and applied voltage is adapted such that the electrical circuit is directed across the electrodes 220 and 230a and 230b through the test fluid 280. FIG. 7b is a top view of the apparatus in FIG. 7a, illustrating the insulated separation of the dielectric surfaces in the container wall of the apparatus.

It should be understood, of course, that the dielectric constant of the insulating material of the container 210 of the system 200 should be lower than that of any liquid phases being tested for wetting on the testing surface. Similarly, it should be understood, of course, that the dielectric constant of the insulating material of the container should be lower than that of the material of the testing surface. A first electrode is placed in electrical contact with the dielectric solid to be tested. This type of apparatus can measure the change in surface wetting on a tested dielectric surface from a first liquid phase to a second liquid phase as a second bulk fluid including the second liquid phase is sheared in the container of the apparatus at a controlled rate for a controlled contact time. The dielectric solid surfaces can be selected to simulate the rock of a subterranean formation in a well. The first liquid phase can simulate a prior oleaginous film formed on the surface of the rock. The second bulk fluid can and conditions of shear and time can simulate the displacement of the oleaginous film by a spacer fluid.

Figure 8:
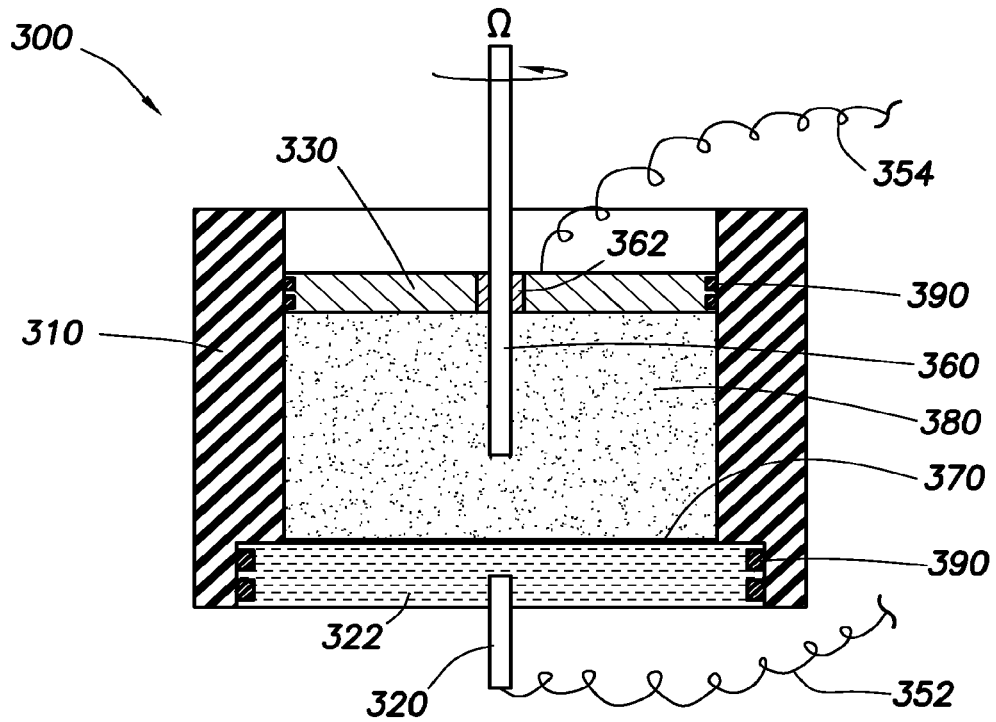
FIG. 8 is a vertical cross-sectional view of an alternative electrical apparatus for measuring the change in surface wetting on a dielectric solid surface, which can be selected, for example, to simulate a rock surface of a subterranean formation.

FIG. 8 is a vertical cross-sectional view of an alternative electrical apparatus 300 for measuring the change in surface wetting on a dielectric solid surface, which can be selected, for example, to simulate a rock surface of a subterranean formation. As illustrated in FIG. 8, in this embodiment the rock surface is axially separated from another electrode exposed to a bulk fluid in the chamber of the container.

As shown in FIG. 8, the electrical system 300 includes: an insulating holder or container 310, a first electrode 320, which is concentrically located in the bottom of a sample of formation material 322; a second electrode 330 toward the top of the apparatus 300, rotational speed Ω (provided by a motor not shown); a plurality of wires including 352 and 354 from the first electrode 320 and second electrode 330 to an EIS measuring device (not shown); a shearing structure 360 extending downward into the container 310; bushings 362 for the stirring rod, and at least one, preferably a plurality, of fluid-tight O-rings 390 between the second electrode 330 and the container.

This system 300 is adapted for simulating and measuring the formation or removal of any wetting or coating or film 370 on the surfaces of the formation material 322 in the presence of a test fluid 380. The changes can be measured under shearing conditions applied to the test fluid 380 in the system 300. The composition of the test fluid 380 can be kept constant during a testing procedure or it can be changed continuously or intermittently by dosing another test fluid that displaces the original fluid under controlled hydrodynamic conditions. In general, the system and applied voltage is adapted such that the electrical circuit is directed across the electrodes 320 and 330 through the test fluid 380.

It should be understood, of course, that the dielectric constant of the insulating material of the container 310 of the electrical system 300 should be higher than that of any liquid phases being tested for wetting on the testing surface. This type of apparatus can measure the change in surface wetting on a tested dielectric surface from a first liquid phase to a second liquid phase as a second bulk fluid including the second liquid phase is sheared in the container of the apparatus at a controlled rate for a controlled contact time. The dielectric solid surfaces can be selected to simulate the rock of a subterranean formation in a well. The first liquid phase can simulate a prior oleaginous film formed on the surface of the rock. The second bulk fluid can and conditions of shear and time can simulate the displacement of the oleaginous film by a spacer fluid.

Figure 9B:
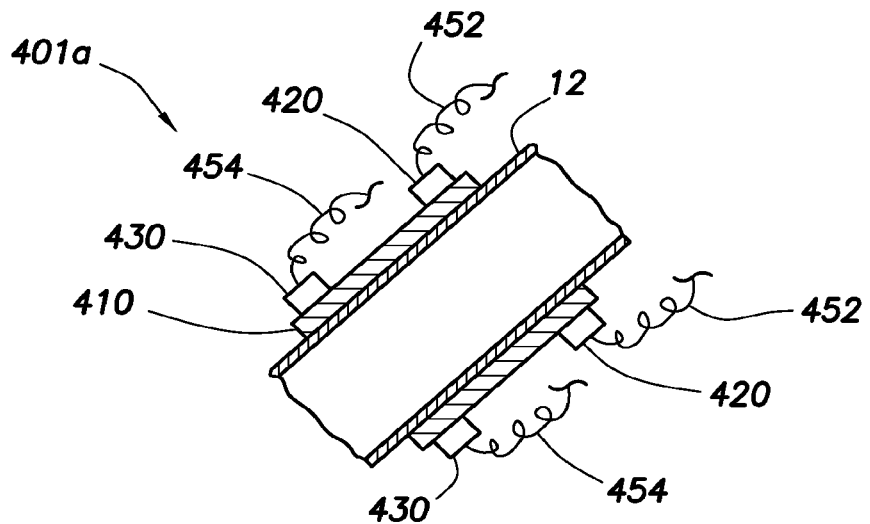
FIGS. 9a and 9b are vertical cross-sectional views illustrating an embodiment depicting direct electrical measurements in a well, which can be used, for example, during the real-time pumping operations to determine any change in wetting of a downhole tubular surface during a well operation such as cementing.
Figure 9A:
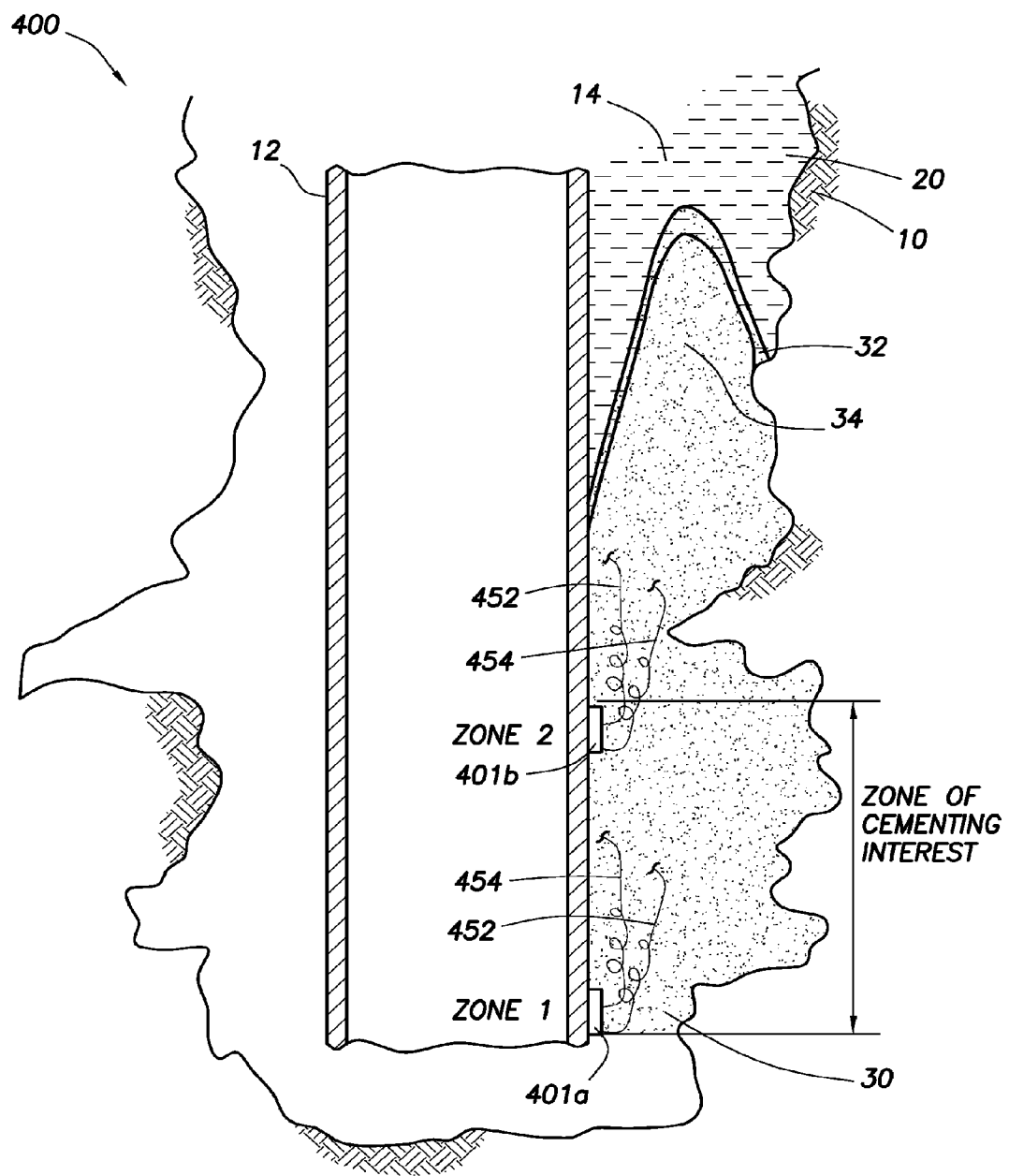

FIGS. 9a and 9b are vertical cross-sectional views illustrating an embodiment depicting direct electrical measurements in a well, which can be used, for example, during the real-time pumping operations to determine any change in wetting of a downhole tubular surface during a well operation such as cementing. FIG. 9a is a vertical cross-sectional view of a portion of a metallic tubular, such as a casing, positioned in a wellbore. FIG. 9b is a detail view of an electrical probe device associated with a portion of the casing in the wellbore. According to this embodiment of the invention, a measurement of the surface wetting of a metallic sample material that is similar to a casing material in the well is obtainable directly situated in the downhole environment.

As shown in FIG. 9a, the system 400 of this embodiment includes: a well penetrating a formation 10, a metallic tubular, such as a casing 12, positioned in the wellbore of the well, which forms an annulus 14 between the outside the casing and the wellbore. Similar to the illustration of the situation in FIG. 2, a drilling mud 20 is shown being displaced by a spacer fluid 30, which during displacement forms a diffused layer 32 and a contaminated spacer fluid layer 34. In this embodiment, there is a zone of cementing interest, that is, a zone for which a good placement and bonding of cement to the metallic surface of the casing 12 is desired. One or more electrical probe devices, such as probe devices 401a and 401b, are operatively deployed adjacent a portion of the casing in or near the zone of cementing interest, for example, at position Zone 1 or position Zone 2. As shown in FIG. 9a, electrically insulated wires 452 and 454 extend uphole to the surface from each of the probe devices 401a and 401b.

FIG. 9b is an illustration of the electrical probe device 401a. Electrical probe device 401b can be substantially similar to electrical probe device 401a. It can be for measurement redundancy or making measurements along more than one position in the zone of cementing interest.

The electrical probe device 401a should be electrically insulated from the metallic casing 12, however, so as to avoid an undesired circuit path. Accordingly, in this embodiment, the probe 401a device includes an electrically insulating sleeve 410 to insulate a first electrode 420 and a second electrode 430 from the metallic casing 12 and to support the first and second electrodes apart from each other in the annulus 14. The first electrode 420 and the second electrode 430 are operatively connected to an EIS measuring device at the surface through insulated electrical wires 452 and 454. It should be understood, of course, that the dielectric constant of the insulating sleeve 410 should be lower than that of any liquid phases being tested for wetting on either of the first electrode 420 or second electrode 430 in the well. Measuring the wetting on the first or second electrodes with EIS can be used to determine the wetting on the adjacent casing.

Electrical Wire and Electrodes

Electrical wire refers to an elongated metallic conductor that is covered with an electrically insulating material. Electrical wire is used to carry electricity.

An electrode is a metallic electrical conductor used to make contact with a non-metallic part of a circuit (e.g. a semiconductor, an electrolyte, or a vacuum).

A first electrode is used in conjunction with a second electrode. In addition, sometimes a reference electrode is used in a three-electrode system.

The first electrode can be an electrode in an electrical system on which the change of interest is occurring. In a two-electrode system, either a known current or potential is applied between the first and second electrodes and the other variable may be measured.

When a three-electrode cell is used, the first or second electrode, along with the reference electrode, provides a circuit over which current is either applied or measured. This configuration allows the potential of the first or second electrode to be measured against a known reference electrode without compromising the stability of the reference electrode by passing current over it.

In measuring for the purposes of determining the changes in an electrical double layer or film on a surface, the electrical system is operated at a current or potential below that which would cause a redox reaction in the chemical species present in the system.

Selecting First Electrode for Downhole Surface to be Simulated

The first electrode is preferably made of the same metallic material as a downhole material, such as a metal tubular, for which any change of water wettability or wetting is to be simulated and determined. The surface of the first electrode can be modified by roughening, polishing, mill varnishing, etc., or it can be a corroded piece of the material, depending on the condition of the downhole tubular to be simulated. The first electrode can be made initially water wetted or oil wetted as desired, to simulate the condition of a downhole surface.

Selecting Second Electrode

The second electrode can be the same as the first electrode, in which case standardization in the experimental method demands that the first electrode and second electrode be machined out of the same piece of stock to ensure the same averaged characteristics on both the electrodes. Alternatively, the second electrode can be made of a non-corrosive conductive material, such as platinum or graphite, as a standard material. For the ability to compare between labs and companies, it would be preferable to use standard materials as the counter electrode and have an option to use specific well materials if desired. Using standard platinum or graphite electrodes as the counter electrode would eliminate the need to change both the electrodes for testing different materials.

Preferably, the surface area, aspect ratio, and surface to volume ratio of each of the first and second electrodes is as close as practical to each other for symmetry in the electrical test system.

Optional Reference Electrode

Preferably, a reference electrode is mounted in the electrical system in close proximity to the first electrode. A reference electrode is an electrode that has a stable and well-known electrode potential. The purpose of the reference electrode is to make sure that the potential of the first electrode remains constant with respect to the ground. This system is analogous to a 3-point potentiostat system.

The reference electrode can be, for example, a standard calomel electrode or an Ag electrode in AgCl solution.

Selecting Test Bulk Fluid

The test bulk fluid can be selected to simulate a well fluid or downhole fluid.

For example, when a water-based spacer fluid is used to displace an oil-based drilling fluid (also known as an oil-based drilling mud) in the annulus prior to pumping cement, a concentration gradient can be clearly noticed at the interface of the spacer fluid and drilling fluid. This concentration gradient is due to mass and momentum transport owing to the differences in densities and rheologies of the bordering fluids, and is better known in the industry by various names, such as intermixing, channeling, and fingering.

A surfactant package of one or more surfactant chemicals is usually included in the water-based spacer fluid to make a stable, water-external emulsion when the water-based fluid mixes with an oil-based fluid, such as an oil-based drilling mud. The surfactant package can include, for example, a combination of: (a) oil-soluble surfactant; (b) water-soluble surfactant; and (c) emulsifier. The surfactants are believed to make the emulsion water external and oil internal.

People skilled in the art of designing cement jobs would appreciate that achieving water wet surfaces downhole is a tradeoff between the surfactant concentrations and contact volumes and concentrations. An initial spacer/mud volume ratio needs to be fixed and the surfactant pack optimization is carried out at that fixed ratio. If a surfactant pack optimization is planned at 25/75 spacer/mud concentration, obviously more surfactant will be needed to make a stable water external emulsion. If it is planned at 75/25 spacer/mud concentration, not enough fully water-wetting spacer is left behind to carry out the cleaning operation.

Previous methods discuss optimizing the surfactant package by testing to achieve full bulk conductivity in the emulsion. When the bulk conductivity of the emulsion remained constant at all shear rates and equal to that of the pure water-based spacer fluid, it was concluded that the emulsion was a stable emulsion and would not invert back to become unstable. This measures the solution bulk resistivity at only a single frequency, typically 50 Hz or 60 Hz, whichever frequency is locally available. This only gives information on the conductivity of the solution alone, but does not give any information about any interfacial phenomena.

Blending of two phases in the bulk of a fluid system under the effect of shear does not complete cleaning on surfaces. For correct design of operational parameters and fluid systems to meet the design intent of achieving complete surface wetting, it is critical to simulate the bulk shear rates and wall shear rates in an experimental setup at the laboratory scale or via pilot testing to be nominally equivalent to the shear rates expected to be experienced downhole.

Interfacial tension of oil-water phases is reduced by fit-for-purpose surface-active agents under shear causes emulsion to be inverted, thereby changing the continuous external phase from oil to water or vice-versa. US Statutory Invention Registration H1932, dated Jan. 2, 2001, entitled "Wettability and Fluid Displacement in a Well." which is incorporated herein by reference in its entirety, discusses methods and apparatuses used for measuring this phenomena by measuring a property related to the electrical conductivity of the emulsion during the inversion process. A drastic change in electrical conductivity is observed when the inversion occurs. The apparatus consists of a blender jar with a blade at the bottom and electrodes that are built into the jar to measure electrical conductivity. However, the deficiencies of that disclosure include: (1) shear rate profiles and distribution are not similar to the wellbore; (2) shear rates are not quantifiable; (3) resolution of the apparatus is not fine enough to capture differences in conductivity with varying percentage of water wetting on the electrodes; (4) electrodes are contact pins that have very low surface area compared to the mixing geometry; (5) the property being measured is a bulk property and not a surface property; and (6) formation surfaces are not adequately simulated because only small metal pins act as electrodes.

For example, a problem with the US H1932 is that although there are two electrodes in the test cup that are insulated from the cup, the cup is made of metal. So for this system, if there is a water wetting of a portion of the seal (or the entire seal behind the electrode), the path of least electrical resistance is not across the fluids to the other electrode, but only about $1/16$ inch from the electrode to the metal mixer container, around the metal container to the second electrode, and then about $1/16$ inch to the second electrode. In a system according to the present invention, the electrodes are larger and fully insulated from the cup so there can be no path between the cup and the electrodes. The conductance (resistance) of the fluid between the electrodes, with additional impedance measurements, are used to measure how much of the electrode is or has become water wet.

It is occasionally noticed, however, that even though full bulk conductivity is achieved, patches of non-aqueous film are still present on the walls of the mixer that is used to carry out the bulk conductivity experiments. US Patent Publication No. 2011/0005310, published Jan. 13, 2011, entitled "Methods for Contacting a Surface with a Fluid Containing a Marker to Determine the Wettability of the Surface," which is incorporated herein by reference in its entirety, discloses a visual inspection method based on a dye to qualitatively study surface wetting. They demonstrated the transition from partially water-wet condition to fully water-wet condition on the surface by increasing the concentration of surfactant package. Unfortunately, the percentages of surface wetting are not easy to measure. It has also been observed that though bulk water wetting is achieved for a particular composition in this set up, there are particles of non-aqueous film on the surface of the jar. Moreover, it is well known from literature that surface wettability depends on the roughness, electrical charge, and reactivity of the surface in question. This patent shows the occurrence of non-aqueous film and describes a visual imaging technique to quantify the same. The challenges associated with visual imaging include: (1) poor repeatability; (2) operator error associated with imaging and photosensitivity; (3) properties of dyes/markers that may interfere with the chemical reactivity of the system; (4) difficulty in performing under High Pressure and High Temperature ("HPHT") conditions; (5) difficulty with imaging while in-situ owing to the presence of particle laden or dirty fluids; (6) difficulty with creating images on surfaces that are curved; (and (7) shear rate values not objective and quantifiable.

According to the present invention, methods and apparatuses are provided that overcomes the challenges associated existing techniques that include: (1) quantifiable shear; (2) HPHT conditions; (3) workability with particle lade or dirty fluids; (4) ability to study the effect of contact time; (5) additional capability to study how much wall shear stress is needed to overcome the surface tension/cohesion/adhesion effects associated with non-polar surface films. These findings can then be applied to job design for determining fluid properties and operational parameters like pump rates and contact times.

To replicate the downhole conditions and to carry out meaningful testing, a concentration ratio needs to be first fixed and hence, the electrolyte is chosen to be a mixture of an oil-based well fluid and a water-based well fluid in the desired concentration. The water-based well fluid can have a known concentration of surfactant package already pre-mixed.

A coating (layer of oil based mud, filter cake, silicate coating, etc.) whose dielectric properties are different from that of the fluid used (inverter fluid or spacer) for cleaning the coating may be pre-applied and the electrolyte can be the pure, uncontaminated inverter or spacer fluid to simulate the flow behavior in the annulus below the diffuse layer. FIGS. 6a-6b, 7a-7b, 8, and 9a-9b show schematic representation of various electrical systems where a film can be applied to a surface and subjected to shear by another bulk fluid for the purposes of measuring changes in wetting on the surface.

Alternately, the fluid that is responsible for creating the coating (drilling mud) may be replaced completely with a wash, spacer or inverter fluid while going through an optional process of generating homogenous admixtures with incremental variation on the volumetric ratios between both the fluids. The electrical properties associated with this setup can be monitored to understand the displacement and the dynamics of coating removal. FIGS. 6a-6b, 7a-7b, 8, and 9a-9b show the schematic representation of electrical systems where the non-aqueous material will be displaced by a water-wetting wash/spacer/inverter-fluid, while facilitating the application of shear and impedance measurement simultaneously.

Impedance Spectroscopy and Modeling

An alternating current electrical potential difference is applied in between the first and second electrodes and the alternating current flowing in between them is measured. The potential difference needs to be at least sufficient to form a measurable electrical circuit through a fluid between the first and second electrode.

The ratio of the voltage to alternating current flowing across the first and second electrodes is termed as impedance. Unlike resistance, which is a simple linear quotient between voltage and current, impedance is a complex number. When this voltage is alternating in nature, and is applied at various frequencies in the range of 1 microHertz to 1 gigaHertz, and the current responses to these frequencies are measured at the respective frequencies, impedances can be calculated in the frequency domain to give crucial information about bulk, interfacial, and electro-kinetic processes in the system.

Figure 10:
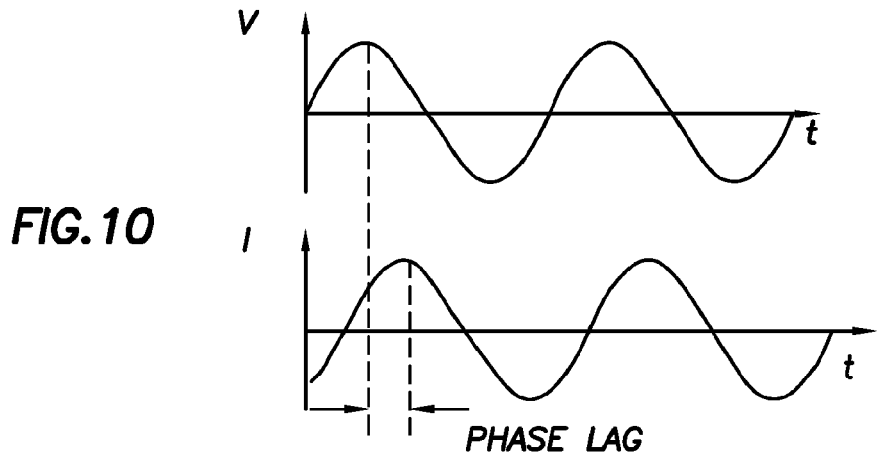
FIG. 10 is a graphical illustration representing voltage (V) and current (I) waveforms in time (t) in a pseudo-linear system, for which the current response to a sinusoidal potential will be a similar sinusoidal signal at the same frequency, but with a lag in phase.

Impedance is measured using a pseudo-linear or small signal response. In a pseudo-linear system, the current response to a sinusoidal potential will be a similar sinusoidal signal at the same frequency, but with a lag in phase as shown in FIG. 10.

The excitation potential is of the form of Equation 2:

$$V = V_0 \sin(\omega t) \quad \text{Eq. 2}$$

where $V_0$ is typically in the range of about 1 mV-100 mV to make it a pseudo-linear system.

Then, the current response signal is of the form of Equation 3:

$$I = I_0 \sin(\omega t + \varphi) \quad \text{Eq. 3}$$

The impedance of the signal can be calculated analogous to Ohm's law as Equation 4:

$$Z = V/I = V_0 \sin(\omega t)/I_0 \sin(\omega t + \varphi) = Z_0 \sin(\omega t)/\sin(\omega t + \varphi) \quad \text{Eq. 4}$$

This is often transformed into the frequency domain to represent in a complex number form and is represented in Equation 5.

$$Z(\omega) = Z_0 \exp(j\varphi) = Z_0(\cos \varphi + j \sin \varphi) \quad \text{Eq. 5}$$

The complex number Z is composed of a real part and an imaginary part. A representation of the imaginary part plotted on the y-axis against the real part of the x-axis, is called the Nyquist plot.

Bode plots represent variation of $|Z|$ and $\varphi$ as a function of $\omega$.

These plots can be analyzed in terms of an equivalent circuit model and model parameters are fitted using Non Linear Regression techniques. Initial guess of the closest applicable model and the values of the capacitance and resistance contributed by individual elements in the system (electrolyte, electrode, and auxiliary connections) can be inferred from the shape and inflexions on the Nyquist and Bode plots.

Figure 11:
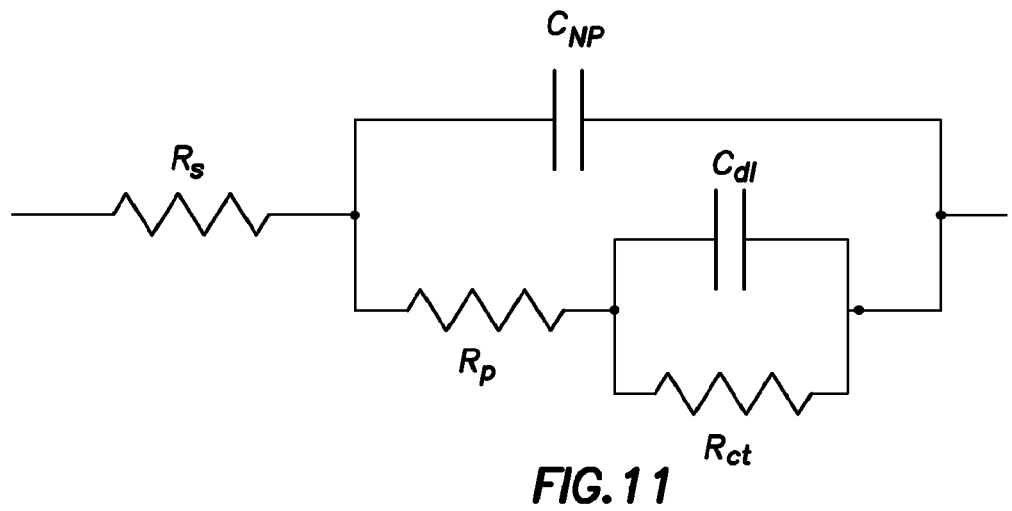
FIG. 11 illustrates an example of a circuit that can be used for impedance modeling in electrical systems.
Figure 12:
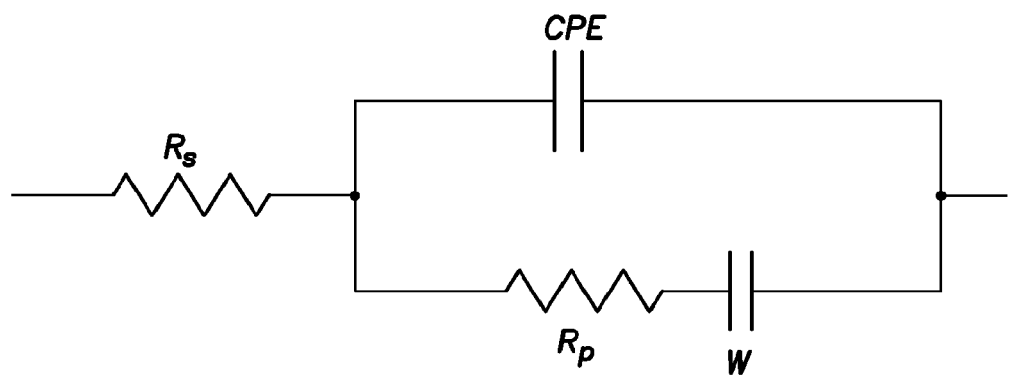
FIG. 12 illustrates an example of a circuit that can be used for impedance modeling in electrical systems.

According to the invention, a technique of impedance spectroscopy is applied to model the wettability or wetting of a metal surface, may be done for example as illustrated in the circuit models shown in FIG. 11 and FIG. 12, where the system includes solution bulk resistance, non-polar layer capacitance, polarization resistance, charge transfer resistance, and double layer capacitance between the surface of the first electrode and the second electrode. Depending on the physical scenario, one of many of these circuit elements may be missing in the equivalent circuit model that best fits the impedance data.

For example, the best fitting equivalent circuit can be a Failed Paint Model (FP) circuit model as shown in FIG. 11 or a Constant Phase Element with Diffusion ("CPED") circuit model as shown in FIG. 12.

Figure 13:
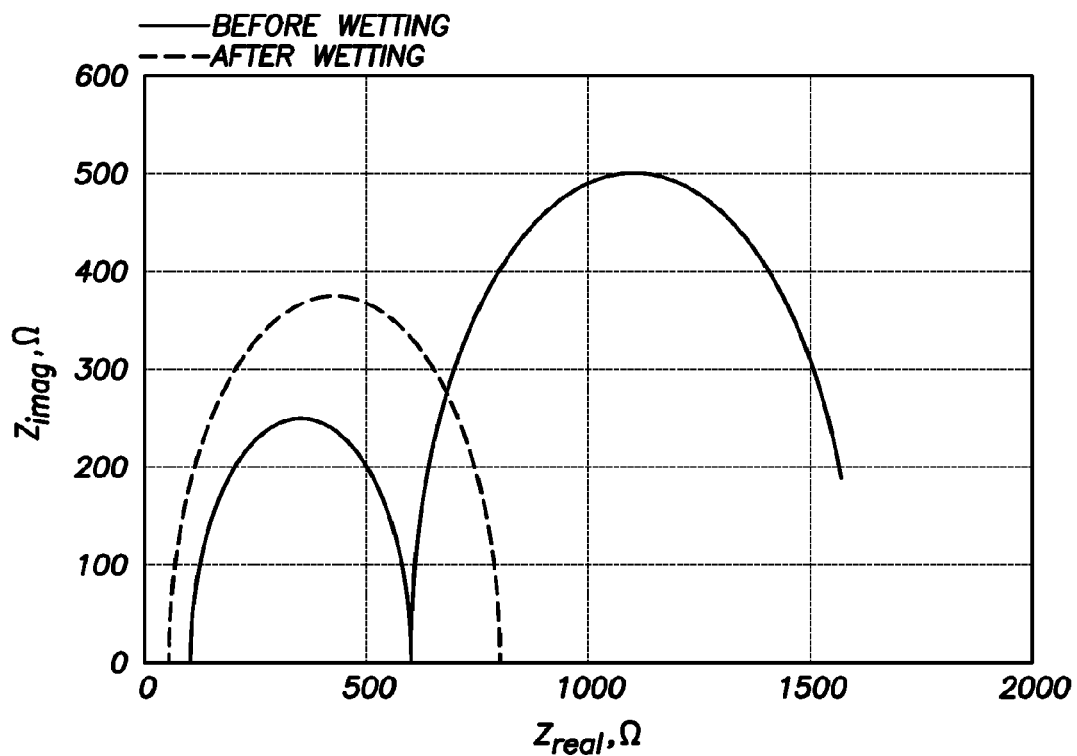
FIG. 13 shows an example of Nyquist plot comparing the impedance data before and after surface wetting with a Failed Paint Model (FP) circuit model as in FIG. 11.
Figure 14:
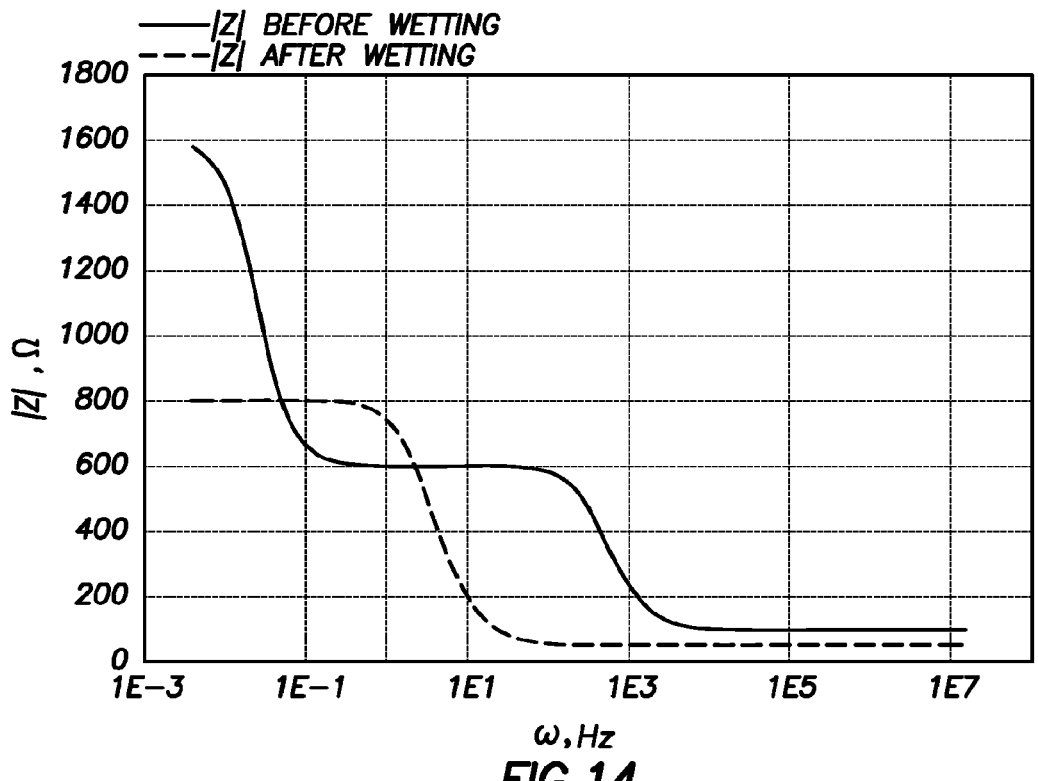
FIG. 14 shows an example of a Bode plot comparing the impedance data before and after surface wetting with a Failed Paint Model (FP) circuit model as in FIG. 11.

From theoretical point of view, as the non-aqueous film gets cleaned from the surface of the electrodes, it is expected that the value of double layer goes up and the other components like charge transfer resistance, or polarization resistance go down. For example, if the best-fit equivalent circuit is Failed Paint Model ("FP") model, then the Nyquist and Bode plots are shown in FIG. 13 and FIG. 14, respectively, depicting the cases of before and after changing an oil-wetted surface to a water-wetted surface.

Figure 15:
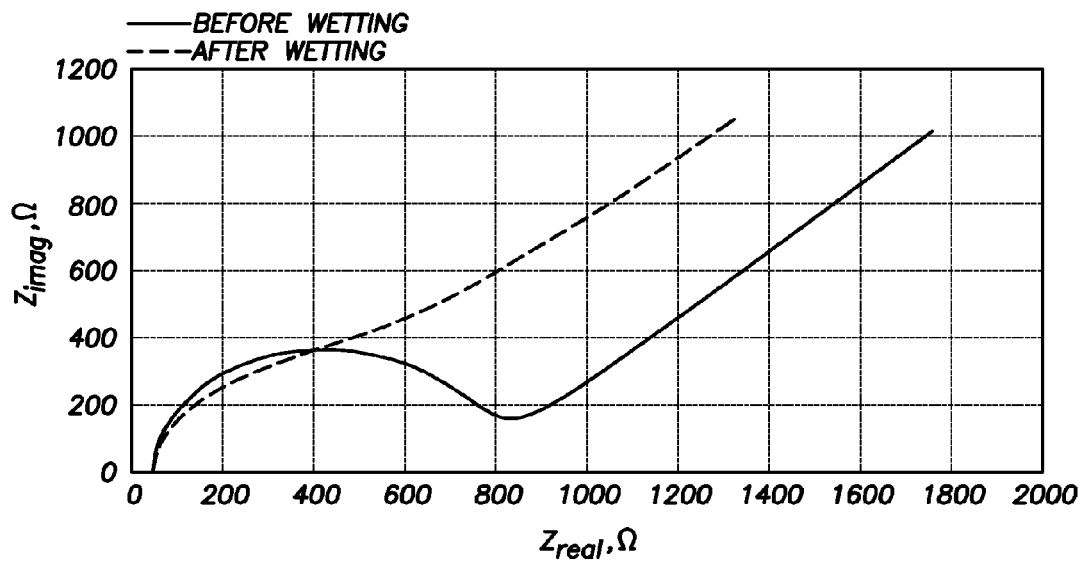
FIG. 15 shows an example of a Nyquist plot comparing the impedance data before and after surface wetting using a Constant Phase Element with Diffusion ("CPED") circuit model as in FIG. 12.
Figure 17:
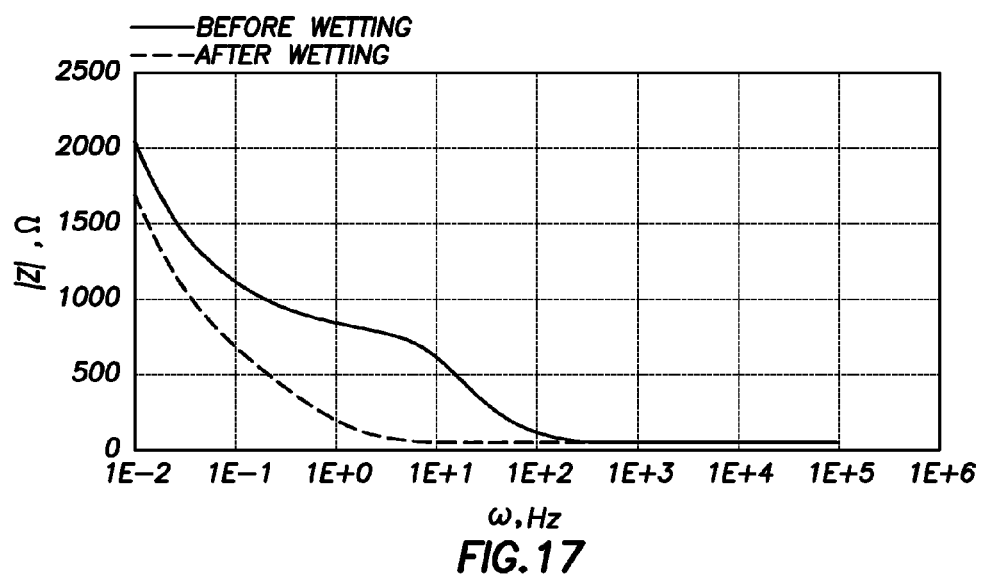
FIG. 17 shows an example of a Bode plot of impedance vs. frequency, before and after surface wetting using a Constant Phase Element with Diffusion ("CPED") circuit model as in FIG. 12.
Figure 16:
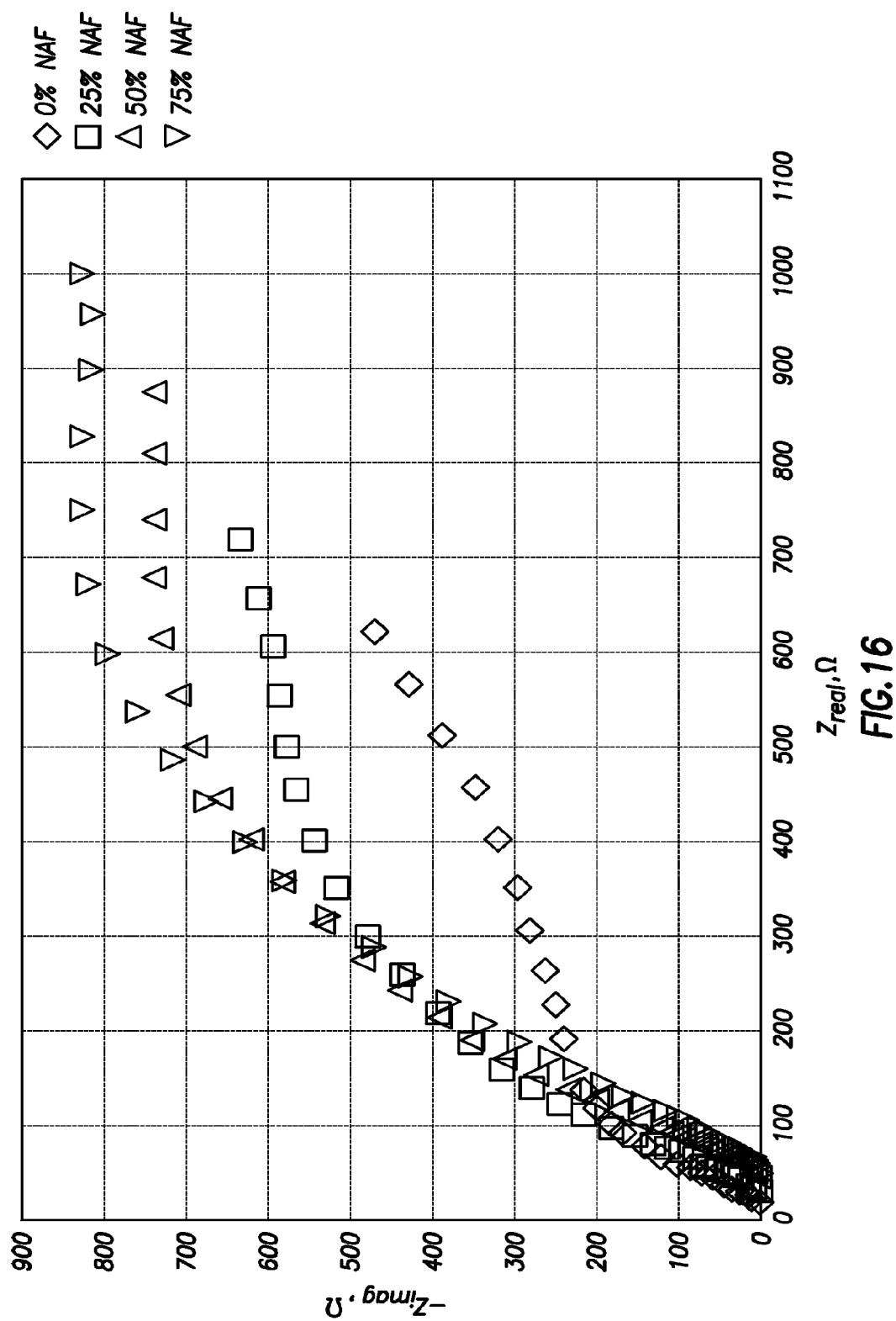
FIG. 16 shows an example of a Nyquist plot from Electrical Impedance Spectroscopy under a no shear condition for different percentage extents of non-aqueous liquid phase coverage, where the non-aqueous film used is an Oil Based Mud ("OBM") made with mineral oil and the electrolyte used is a water-based inverter fluid.

An example of a Nyquist plot according to a CPED model before and after wetting is shown in FIG. 15. Experimentally, a similar variation of Nyquist plot is observed for varying fractional surface covered with non-aqueous film ("NAF"), as shown in FIG. 16. An example of a Bode magnitude plot according to a CPED model before and after water-wetting is shown in FIG. 17. Experimentally, a similar variation of Bode magnitude plot is observed for varying fractional surface covered with non-aqueous film ("NAF"), as shown in FIG. 18.

Figure 18:
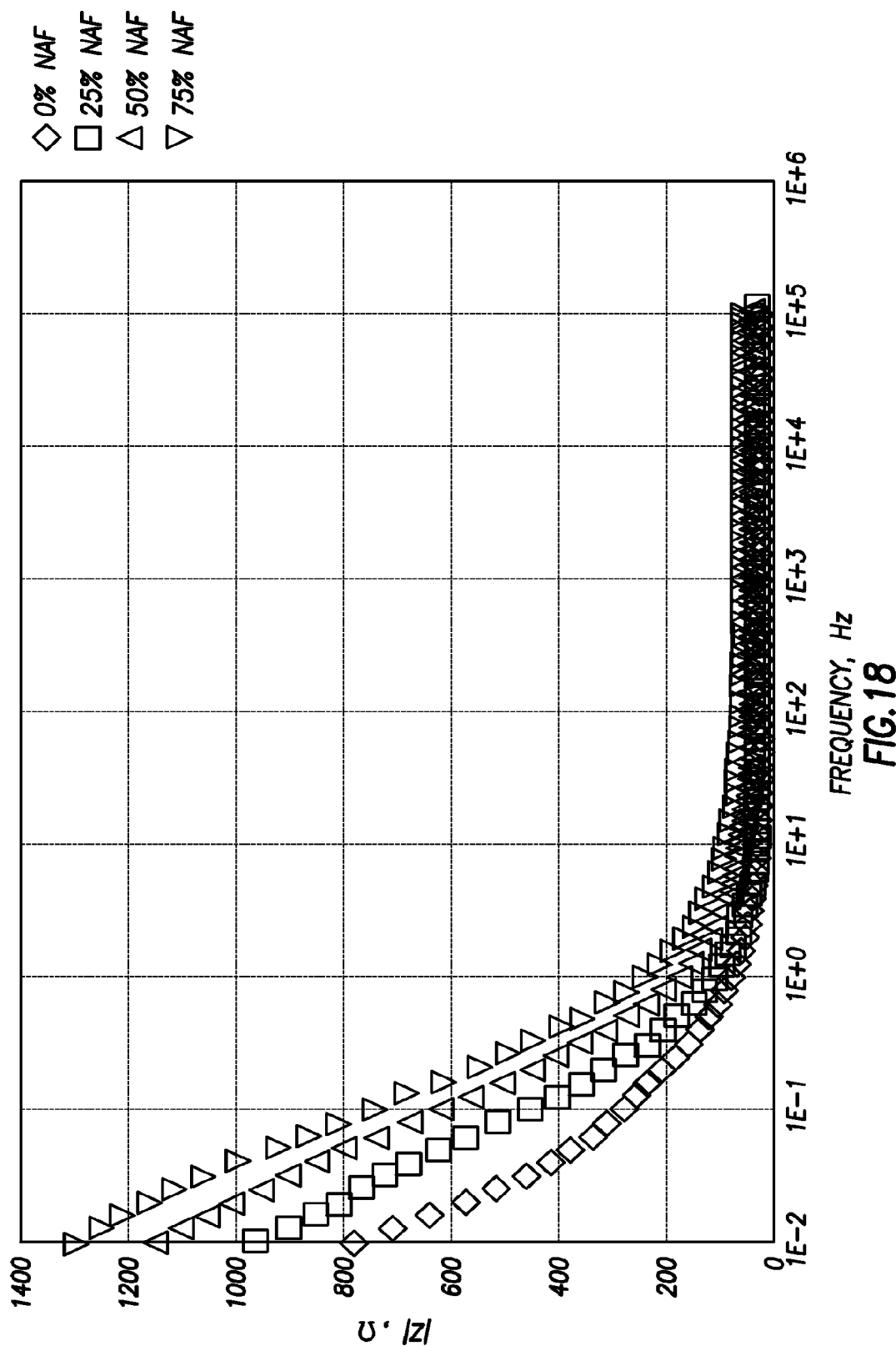
FIG. 18 shows a Bode magnitude plot from Electrical Impedance Spectroscopy for different extents of non-aqueous film coverage corresponding to the Nyquist plot in FIG. 16.

It can be seen from FIG. 16 and FIG. 18 that, as the percent coverage of non-aqueous film increases, the magnitude of impedance increased proportionately. In addition, the CPED model is found to fit the data through EIS modeling and the double layer capacitance, as obtained from the analysis, decreased linearly as the percent coverage of non-aqueous film coverage is increased.

As the fraction of electrode surface that is coated with non-water-wetting film increases, we expect the capacitance reading shown by an LCR meter to reduce linearly because the double-layer capacitance is a surface phenomenon, which occurs at charged surfaces in contact with conducting interfaces.

Figure 19:
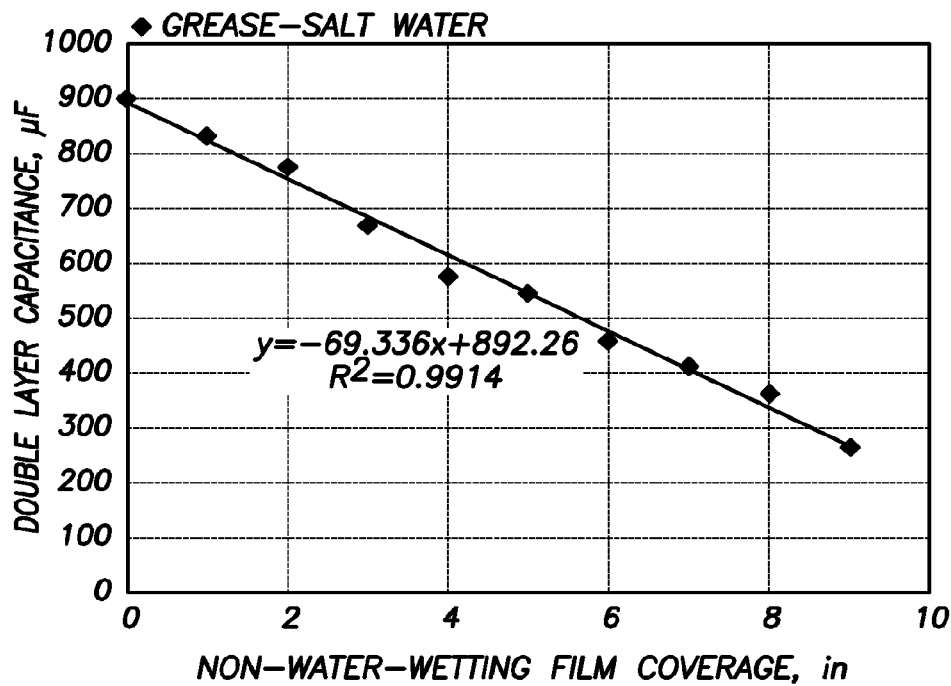
FIG. 19 is a graph of double layer capacitance vs. non-oil-wetting film coverage for a grease and salt-water combination.
Figure 20:
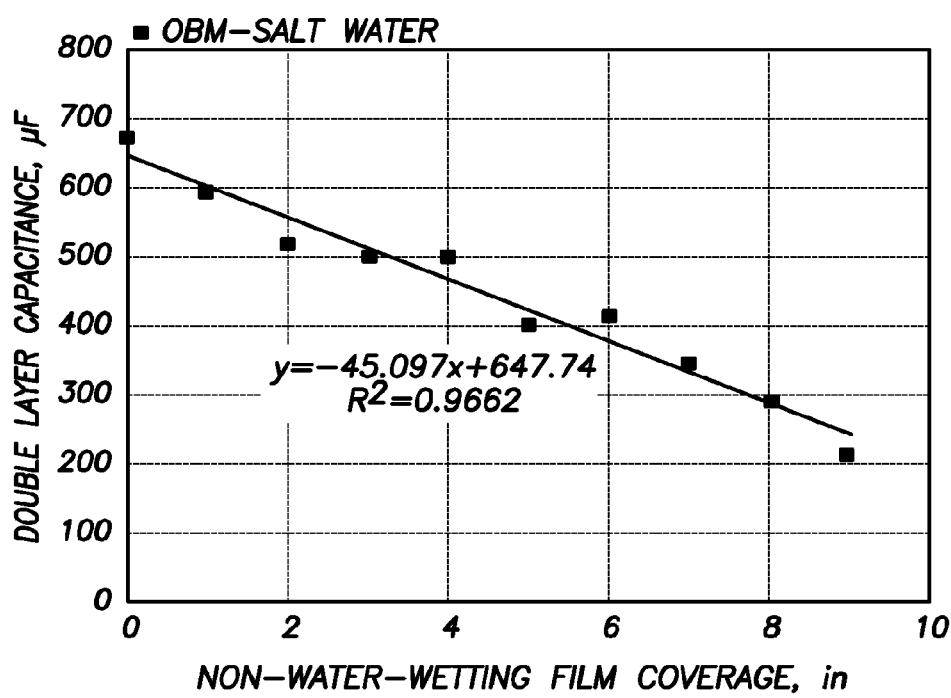
FIG. 20 is a graph of double layer capacitance vs. non-oil-wetting film coverage for OBM and salt-water combination.

The following two combinations of non-aqueous-film and electrolyte were studied in the above-described manner: (a) grease as film and salt-water solution as electrolyte, as shown in FIG. 19; (b) oil-based mud as film and salt-water solution as electrolyte, as shown in FIG. 20. The measured capacitance is plotted as a function of percent coverage of non-aqueous film on the electrode. All the above three combinations are found to follow a linear trend, all having a least squares fit ($R^2$) better than 0.99, as shown in FIGS. 19-20.

This shows that the capacitance can be used as an indirect measure of the surface wettability or wetting.

To account for non-ideal effects, the combination of charge transfer resistance and double layer capacitance may be modeled using a constant phase element (a) following the Equation 6:

$$Z_1(\omega) = \frac{R_{ct}}{1 + (j\omega R_{ct} C_{dl})^\alpha} \qquad \text{Eq. 6}$$

With increase in surface water wetting, when such a model is used, it is expected that the values of double layer capacitance and capacitance used to model the non-polar layer will sharply increase due to increasing efficiency of polarization and appearance of opposite charges near the electrode. The value of polarization resistance and charge transfer resistance is expected to decrease sharply.

The value of the solution bulk resistivity is expected to remain constant from the point any mixture of a water-based fluid and an oil-based fluid forms an emulsion that becomes completely water external while other parameters change during the course of the surface wetting operation. If the electrolyte is changed by forming admixtures with incremental concentration levels during the process of displacing one fluid with the other, all parameters are expected to change—therefore a "control experiment" needs to be carried out to determine the electrical parameters of a system with no coating and pure fluid in place. The values derived during the course of the experiments will then need to be compared with the control experiment in order to determine whether a fully wet surface with a well fluid has been achieved. It should be understood that the well fluid can be, for example, a pure a wash fluid, an inverter fluid, a spacer fluid, or a lead cement composition.

The magnitude of the frequency directly relates to the time scale of species and charge transport. As an example, the bulk transport of mass and charge correspond to time scales of $10^{-6}$ sec and are therefore inferred at high frequencies. It can be seen that corrosion, which is a "long term" process, can be predicted at low frequencies that correspond to time scales of the order of 1000 seconds.

For example, when the technique is used with cement slurry electrolyte, the high frequency response (kHz-MHz) may be used to infer conclusions about the bulk parameters like bulk conductivity, diffusivity, and permeability of the cement paste. The intermediate frequency (Hz-kHz) data may be analyzed to provide information about the nature of the near interface zone and the formation of any porous diffuse layer (oxide/carbonate film, etc.) on the first electrode. The low frequency response (mHz-Hz) provides information on the passive behavior of the steel and corrosion related electro-kinetic reactions.

Figure 21:
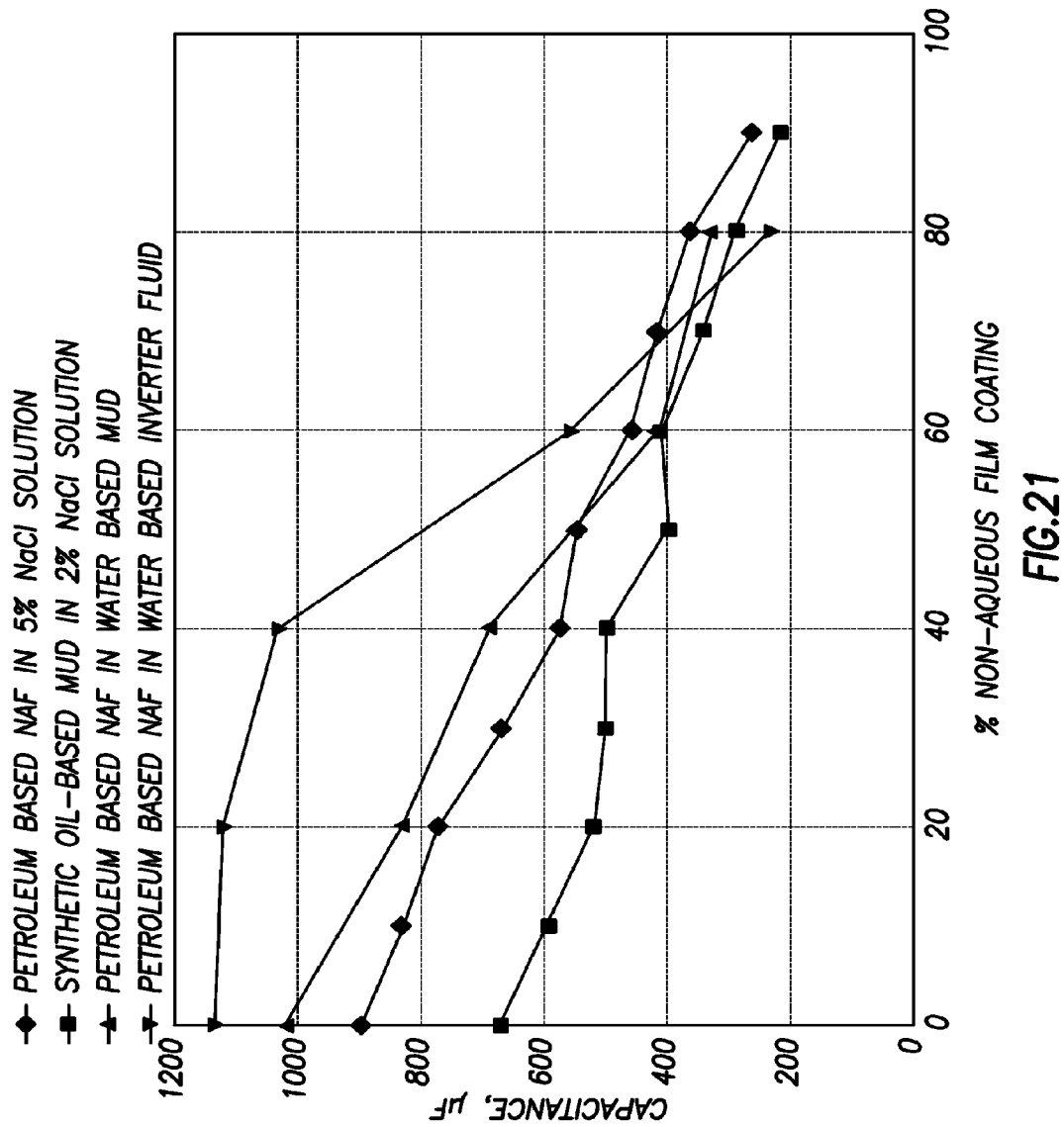
FIG. 21 is a graph of inferred double-layer capacitance vs. percent coverage of several different combinations of non-aqueous films in water-based bulk fluids from electrical measurements in an electrical cell using an identical first electrode and second electrode.

FIG. 21 is a graph of inferred double-layer capacitance vs. percent coverage of several different combinations of non-aqueous films in water-based bulk fluids from electrical measurements in an electrical cell using an identical first electrode and second electrode.

In a similar kind of system to that shown in FIG. 6a, a cylindrical nylon block is machined into a tubular shape and two electrodes are embedded on the inner side of it. A spacer fluid is poured into the nylon block, and impedance data is collected. Spacer fluid is removed and the nylon block is cleaned. A layer of non-aqueous film is placed on the electrodes, and before filling the nylon block with fresh spacer fluid and impedance data is collected. Impedance data collection is repeated, after regular intervals of shear (applied using a cylindrical rod inserted into the fluid, and rotated by using a motor).

Figure 22:
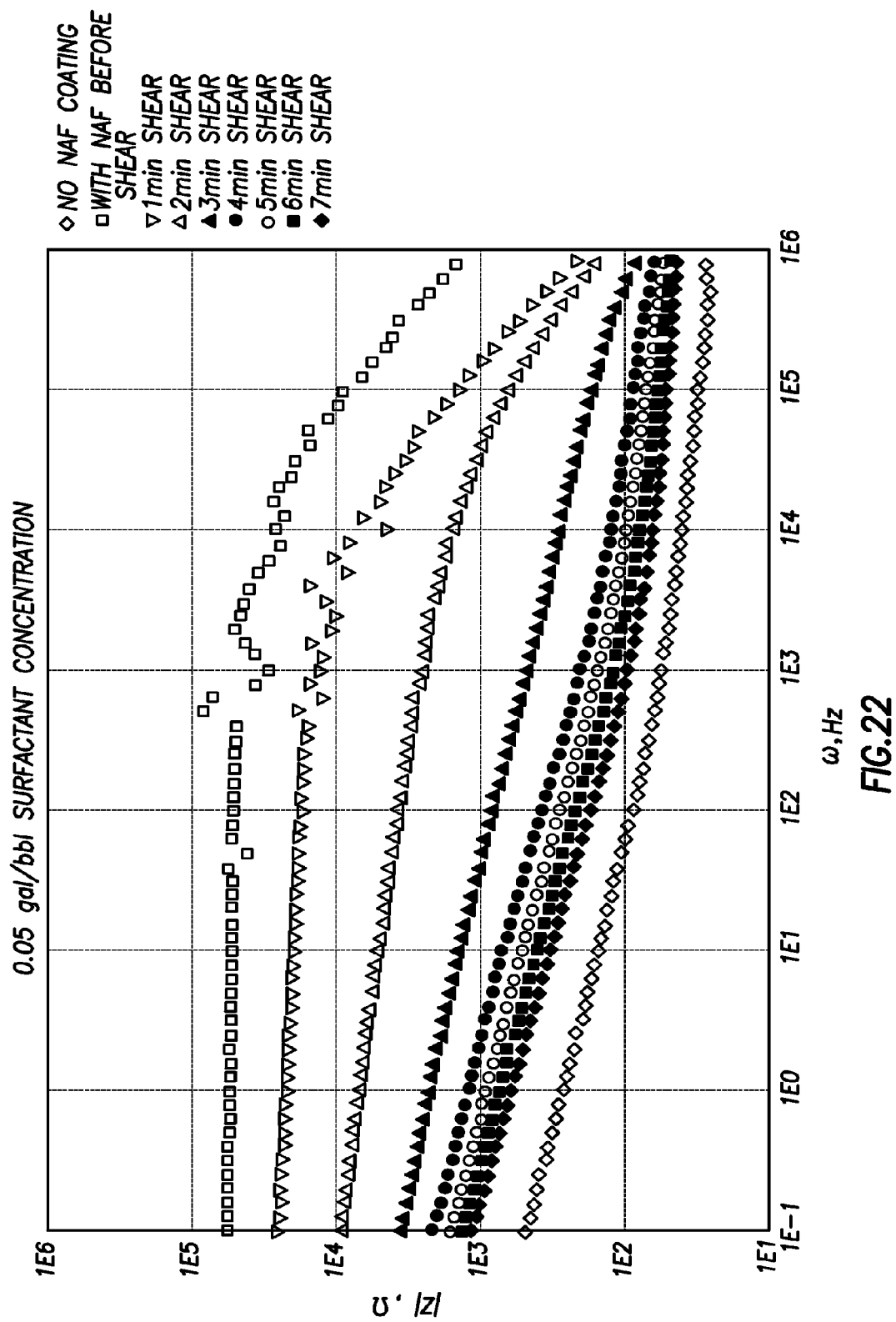
FIG. 22 shows Bode magnitude plots at different durations of shear for the measuring of the effect of contact time with 0.05 gal/bbl surfactant concentration in an aqueous bulk spacer fluid, where the surfactant is an equiproportional mixture of surfactants including alcohol ether sulfate, a low hydrolipic balance non-ionic nonylphenol, and a high hydrolipic balance non-ionic nonylphenol, after following the steps of: (1) placing a spacer fluid in the test cell and taking EIS measurement; (2) starting from a state where the electrodes are coated with non-aqueous film and the test cell is filled with the spacer fluid at no shear and taking EIS measurements; and (3) shear is applied by rotating a cylindrical bob at 900 RPM in a configuration similar to as shown in FIGS. 6a and 6b and EIS data is recorded at intermittent times of 1 minute increments from 1 minute to 7 minutes.

FIG. 22 shows Bode magnitude plots at different durations of shear for the measuring of the effect of contact time with 0.05 gal/bbl surfactant concentration in an aqueous bulk spacer fluid, where the surfactant is an equiproportional mixture of surfactants including alcohol ether sulfate, a low hydrolipic balance non-ionic nonylphenol, and a high hydrolipic balance non-ionic nonylphenol, after following the steps of: (1) placing a spacer fluid in the test cell and taking EIS measurement; (2) starting from a state where the electrodes are coated with non-aqueous film and the test cell is filled with the spacer fluid at no shear and taking EIS measurements; and (3) shear is applied by rotating a cylindrical bob at 900 RPM in a configuration similar to as shown in FIGS. 6a and 6b and EIS data is recorded at intermittent times of 1 minute increments from 1 minute to 7 minutes.

It is observed in FIG. 22 that as the shearing process is continued, the impedance data approached that of a system where there is no non-aqueous film. This is additional evidence that shows this technique can be used to measure the surface wettability or wetting. It is anticipated to take these experiments to the next level by simulating shear at ambient conditions and at high-pressure high-temperature conditions to simulate downhole conditions in a well.

Figure 23:
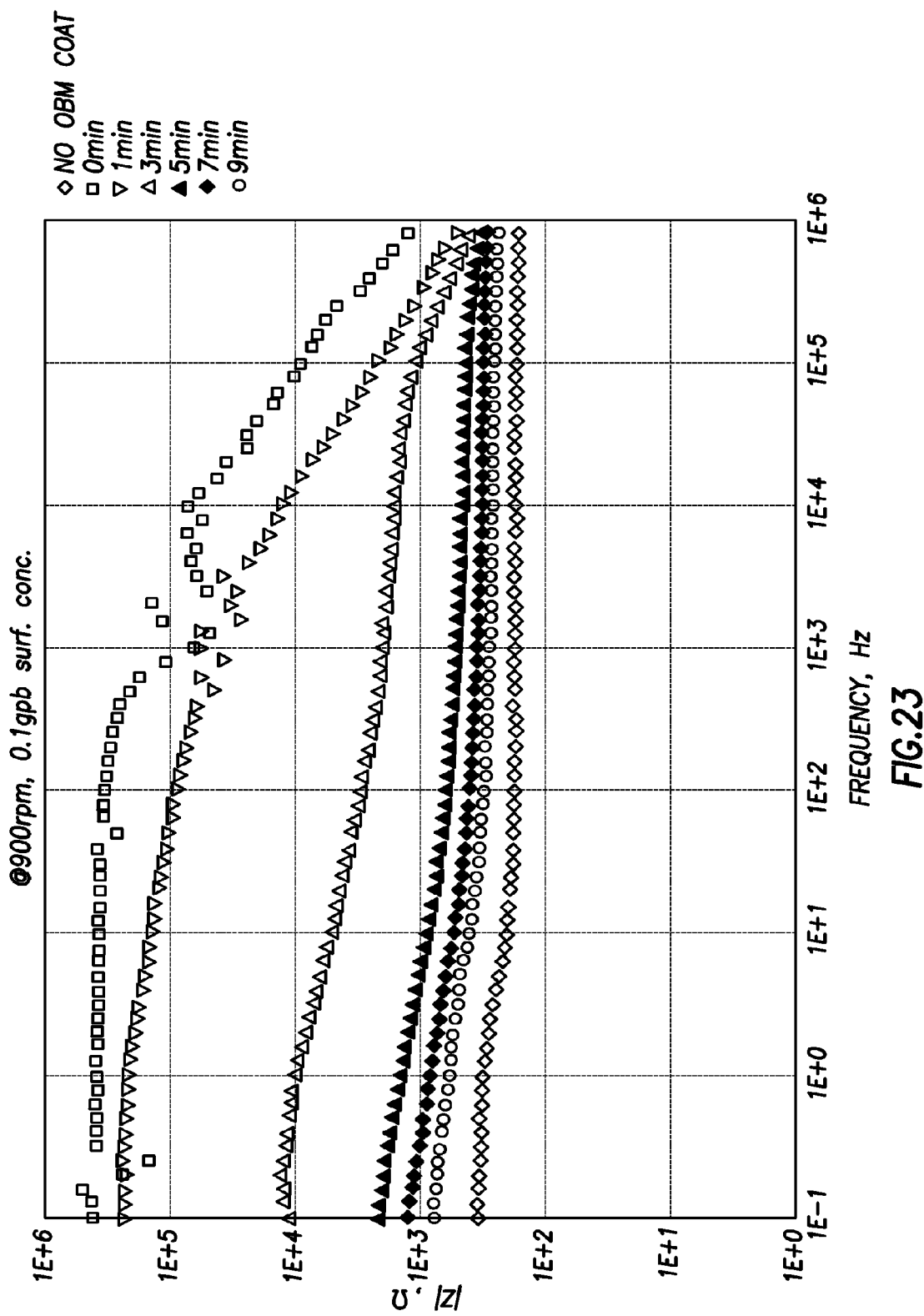
FIG. 23 shows Bode magnitude plots for the experiment in FIG. 22 repeated with 0.1 gal/bbl surfactant concentration.

FIG. 23 shows Bode magnitude plots for the experiment in FIG. 22 repeated with 0.1 gal/bbl surfactant concentration.

Figure 24:
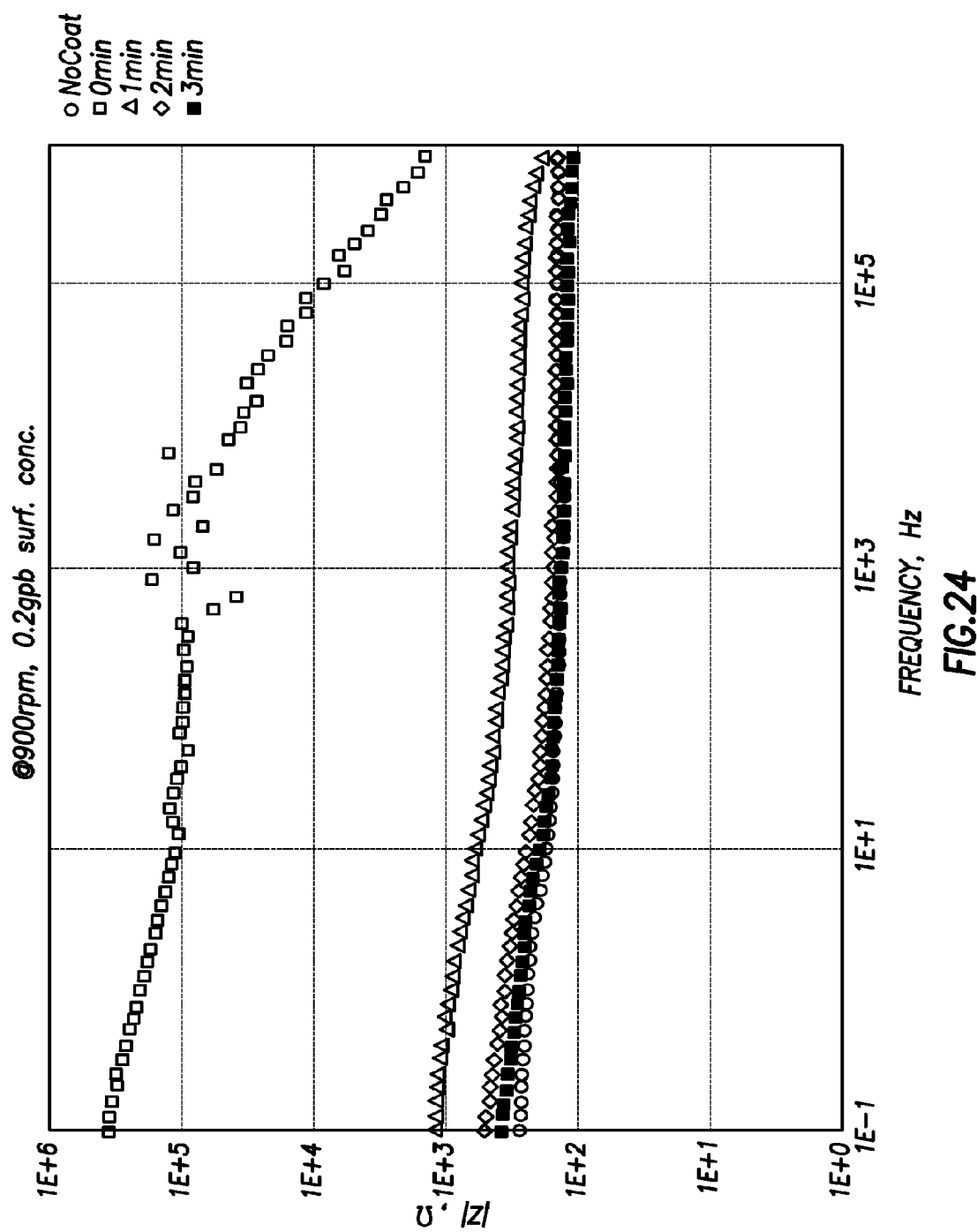
FIG. 24 shows Bode magnitude plots for Experiment in FIG. 22 repeated with 0.2 gal/bbl surfactant concentration, at intermittent times of 1-minute increments from 1 minute to 3 minutes.

FIG. 24 shows Bode magnitude plots for Experiment in FIG. 22 repeated with 0.2 gal/bbl surfactant concentration, at intermittent times of 1-minute increments from 1 minute to 3 minutes.

Figure 25:
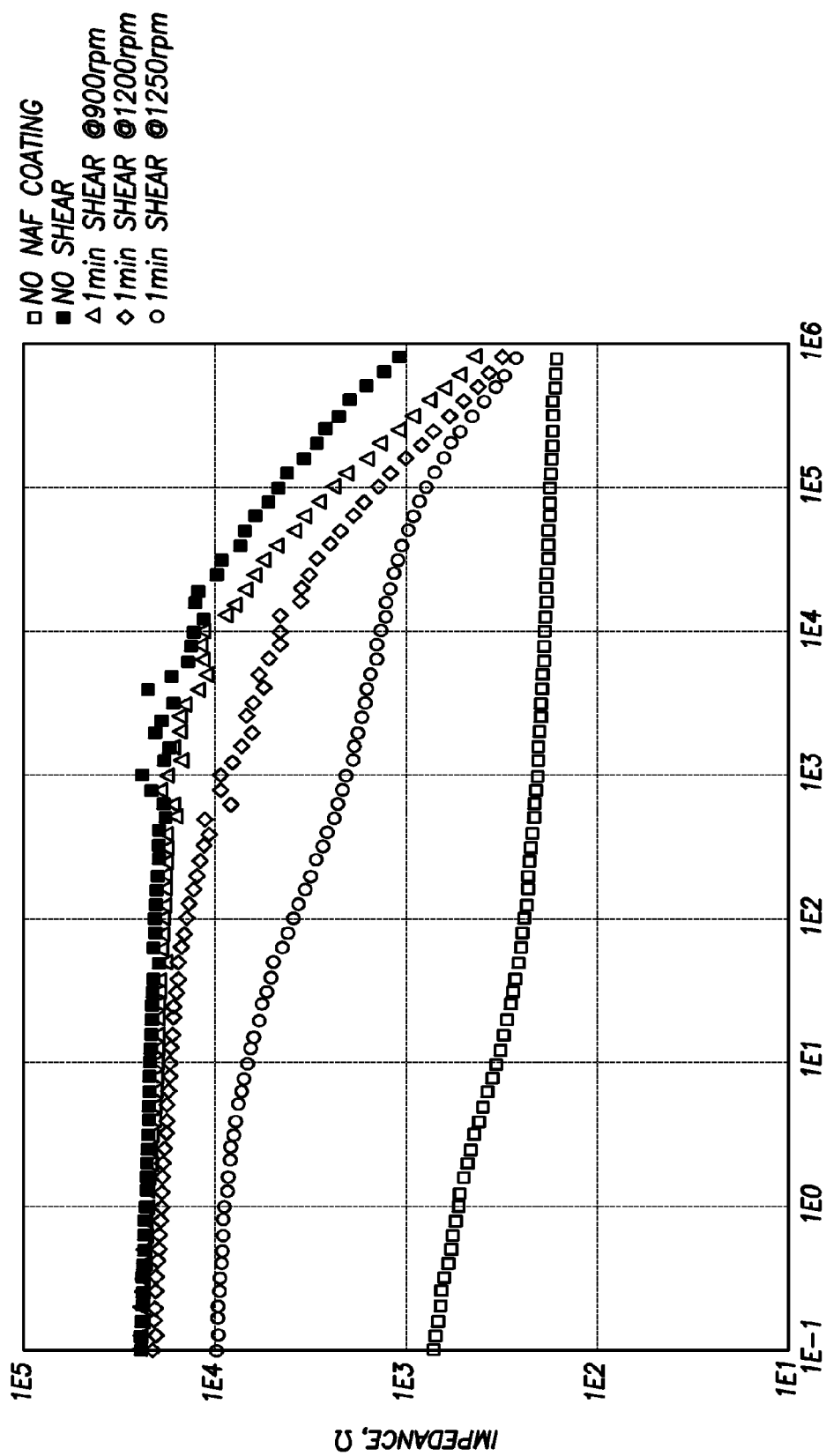
FIG. 25 shows experimental Bode magnitude plots showing the effect of shear rates after following the steps of: (1) placing pure spacer fluid in the test cell and taking EIS measurement; (2) starting from a state where the electrodes are coated with non-aqueous film and the test cell is filled with the spacer fluid at no shear and taking EIS measurements; and (3) shear is applied by rotating a cylindrical bob for 60 seconds at different RPMs of 900 RPM, 1200 RPM, and 1250 RPM in a configuration similar to the apparatus illustrated in FIGS. 6a and 6b and EIS data is recorded at 1 minute.

FIG. 25 shows experimental Bode magnitude plots showing the effect of shear rates after following the steps of: (1) placing pure spacer fluid in the test cell and taking EIS measurement; (2) starting from a state where the electrodes are coated with non-aqueous film and the test cell is filled with the spacer fluid at no shear and taking EIS measurements; and (3) shear is applied by rotating a cylindrical bob for 60 seconds at different RPMs of 900 RPM, 1200 RPM, and 1250 RPM in a configuration similar to the apparatus illustrated in FIGS. 6a and 6b and EIS data is recorded at 1 minute.

Hence, it is believed that impedance spectroscopy can be applied as a technique to gain information about interface and electro-kinetic effects. It is believed this technique can be extended to study the dielectric response of surfaces and porous and conducting formations.

Additional Embodiments of Methods and Apparatuses

According to an embodiment of the invention, a method is provided, wherein the method includes the steps of:

(A) selecting a test material for a surface to be wetted;

(B) selecting a test bulk fluid;

(C) testing a system of the test material and the test bulk fluid with impedance spectroscopy to determine the surface wettability or wetting of the test material with the test bulk fluid under conditions that simulate downhole well conditions.

The testing can be conducted at any convenient location, including in a remote laboratory or in the field at or near the well site.

More particularly according to a preferred embodiment of the invention, a method is provided including the steps of: provided including the steps of:

(A) obtaining or providing an apparatus comprising:
(i) a container forming a chamber;
(ii) a first surface exposed to or in the chamber, wherein the first surface is of:
(a) a first electrode, or
(b) a first dielectric solid material in contact with the first electrode;
(iii) a second surface exposed to or in the chamber, wherein the second surface is of:
(a) a second electrode, or
(b) a second dielectric solid material in contact with the second electrode;
wherein the first surface is electrically insulated from the second surface;
(B) wetting at least the first surface with a first liquid phase of a first bulk fluid;
(C) after the step of wetting, introducing a second bulk fluid into the chamber, wherein the second bulk fluid comprises a second liquid phase, and wherein the second liquid phase is immiscible with the first liquid phase;
(D) applying a second shear between the second bulk fluid in the chamber and at least the first surface; and
(E) making an electrical impedance spectroscopy measurement between the first and second electrode.

According to another preferred embodiment of this method, it includes the steps of: before the step of applying the shear, making a first electrical impedance spectroscopy measurement between the first and second electrode; during or after the step of applying the shear, making a second electrical impedance spectroscopy measurement between the first and second electrode; comparing the first electrical impedance spectroscopy measurement to the second electrical impedance spectroscopy measurement; and based on the step of comparing, inferring any changes in the wetting of the first surface. Preferably, the step of inferring comprises assuming an equivalent electrical circuit model to match experimental impedance changes using non-linear regression techniques.

According to a presently most preferred embodiment, the step of taking an electrical impedance spectroscopy measurement includes: operatively connecting an alternating electrical potential source between the first and second electrodes; while operatively connected to the first and second electrodes, varying the electrical potential or the frequency of the alternating electrical potential source; and while varying the electrical potential or the frequency of the alternating electrical potential source, measuring electrical impedance between the first electrode and second electrode to obtain an electrical impedance spectroscopy measurement.

According to yet another embodiment of this method, the method additionally includes the step of: designing a composition of a first well fluid or conditions of introducing the first well fluid into a well to achieve a change in wetting of a downhole surface in the well.

According to a further embodiment of the above method, the method additionally includes the step of: introducing the first well fluid into the well, wherein the well fluid and conditions of introducing are designed to achieve the desired change in wetting of a downhole surface in the well.

According to a further embodiment of the above method, the method additionally includes the step of: after introducing the first well fluid into the well, introducing a second well fluid into the well to reach the downhole surface in the well.

According to an embodiment, the apparatus of the method includes a reference electrode and the method includes the step of operatively connecting the alternating electrical potential source to the reference electrode.

In an embodiment, the chamber is cylindrical. In another embodiment, the first surface is curved. Preferably, the geometry of the chamber and the first surface simulate the geometry of a surface in a well.

In an embodiment, the first surface is oil-wettable. In another embodiment, the first surface is water-wettable. The first surface can be both oil-wettable and water-wettable, such that wetting with one blocks the surface wettability to another.

In an embodiment, the first surface is of the first electrode and the first electrode is selected to be the same material as a metallic tubular used in a well.

In another embodiment, the first surface is of the first dielectric solid material, and wherein the first dielectric solid material comprises a filter cake, a polymeric material, or any combination thereof. In yet another embodiment, the first surface is of the first dielectric solid material and the first dielectric solid material comprises a rock material. The rock material can be or comprise a sedimentary rock. Preferably, the rock material is selected to simulate a downhole subterranean formation in a well. In such an embodiment, the rock can be saturated with the first liquid phase fluid. This could be used, for example, to simulate a rock surface in a well that is wetted with such a liquid phase.

It should be understood that a material of the first surface can be different than a material of the second surface. For example, the first surface can be of the first dielectric solid material and the second surface can be of the second electrode. It should also be understood that a material of the first surface can be the same as a material of the second surface. In another embodiment, the second surface is of the second dielectric solid material and the second dielectric solid material is the same material as the first dielectric solid material.

In an embodiment, the step of wetting with the first liquid phase includes: (i) introducing a first bulk fluid into the chamber, wherein the first bulk fluid comprises the first liquid phase; and (ii) applying a first shear between the first fluid in the chamber and at least the first surface.

According to an embodiment, the first liquid phase is a dielectric. According to another embodiment, the first liquid phase is oleaginous. For example, the first liquid phase can be the oil of an oil-based drilling mud used in a well.

According to an embodiment, the second liquid phase has a dielectric constant at least 10% different from the dielectric constant of the first liquid phase.

According to an embodiment, the second liquid phase includes water. In this embodiment, the second liquid phase preferably includes an electrolyte. In an embodiment, the second liquid phase is the continuous phase of the second bulk fluid. In yet another embodiment, the second bulk fluid can be an emulsion of the first liquid phase and the second liquid phase. For example, the second bulk fluid can be an oil-in-water emulsion.

In an embodiment, the second bulk fluid includes various other components. For example, in a preferred embodiment, the second bulk fluid includes a surfactant. In an embodiment, the second bulk fluid can include a solid particulate. The solid particulate can help remove a prior film on the first surface by abrasive action during shearing between the first surface and the second bulk fluid. In another embodiment, the second bulk fluid includes a chemical leaching agent for attacking the first dielectric solid material. In yet another embodiment, the second bulk fluid is a foam. For example, the bulk fluid can be foamed or energized with nitrogen gas.

It should be understood that well fluids to be simulated according to the methods of the invention can have widely ranging bulk density. For example, in an embodiment the second bulk fluid can have a bulk density anywhere in the range of 4 ppg to 25 ppg.

In an embodiment, the second bulk fluid is a spacer fluid for use in a well. The composition of the second bulk fluid can be changed during shear to simulate fingering, mixing, or channeling during the introducing of such a well fluid into a well.

In an embodiment of the methods, the change in voltage of the alternating electric potential source is in a pseudolinear range. It should be understood that a pseudolinear range means that if $V_1$ gives $I_1$ and $V_2$ gives $I_2$, then $V_1+V_2$ should give $I_1+I_2$.

In an embodiment of the methods, the change in frequency of the alternating electric potential source is anywhere in the range of 1 microHertz to 1 gigaHertz.

In yet another embodiment of the methods, the current measured for determining electrical impedance has the same frequency as the alternating electric potential source but a shifted phase.

In an application of the methods, the second bulk fluid can be tested for the design shear and design time for a well fluid in a well, such as for a spacer fluid.

In an embodiment, the methods additionally include the step of: controlling the temperature of the second bulk fluid in the chamber. For example, the step of controlling the temperature of the second bulk fluid in the chamber can include controlling the temperature to be the design temperature for a well fluid in a well. It should be understood that controlling the temperature can include heating the fluid while in the chamber.

In an embodiment, the methods can additionally include the step of: controlling the pressure of the second bulk fluid in the chamber. For example, the step of controlling the pressure of the second bulk fluid in the chamber can include controlling the pressure to be the design pressure for a well fluid in a well. It should be understood that controlling the pressure can include pressurizing the fluid while in the chamber.

In an embodiment, the step of inferring comprises assuming an equivalent electrical circuit model for the first electrical impedance spectroscopy and second electrical impedance spectroscopy to match experimental impedance changes using non-linear regression techniques.

Preferably, the wetting of first surface is determined as a percentage of the surface that is water-wetted or oil-wetted. For example, the wetting of the first surface in the bulk fluid is determined as a percentage of the first surface that is water wet at: (a) the beginning of the contact time at the contact shear of the bulk fluid; and (b) the end of the contact time at the contact shear of the bulk fluid.

According to an embodiment, the design conditions of introducing the first well fluid into the well include any one of the following: design volume, design shear, design temperature, design pressure, and design pumping time.

In an embodiment, the test fluid is a water-based fluid. For example, the test fluid can be an oil-in-water emulsion. In an embodiment, the oil-in-water emulsion simulates a downhole fluid that results from the mixing of a prior oil-based drilling mud with a spacer fluid that is for changing the wetting of downhole tubular surfaces from oil-wetted to water-wetted before cementing.

In an embodiment where the test material is selected for being similar in substance to a substance of a solid surface in a well, the test fluid is selected for having the design composition of a downhole fluid to be contacted with the solid surface in the well. For example, the downhole fluid is a water-based fluid, such as an oil-in-water emulsion. In some applications, the downhole fluid is a water-in-oil emulsion.

In a preferred embodiment, the system is tested under similar design conditions as the solid surface in the well and the downhole fluid, including at least the design conditions of temperature, fluid contact shear, and fluid contact time at the fluid contact shear. Where the system of the test material and the test fluid is tested under similar downhole conditions as the solid surface in the well and the downhole fluid, the method preferably additionally includes at least the design condition of fluid contact pressure. In an embodiment, the wettability or wetting of the test material in the test fluid is determined as a percentage of the surface that is water-wetted or oil-wetted. Other parameters can additionally be simulated, such as well fluid volume and downhole mixing with another fluid. Preferably, the wetting of the test material in the test fluid is determined as a percentage of the surface that is water wet or oil wet at: (a) the beginning of the fluid contact time at the fluid contact shear; and (b) the end of the fluid contact time at the fluid contact shear.

In an additional embodiment, wetting of the test material is compared at intermediate fluid compositions made with predetermined concentrations of a first oil based fluid, a second water based fluid spacer/wash/inverter-fluid/lead cement slurry with the "control wetting" of the surfaces with the pure second water based fluid. It can be appreciated that the first fluid may be water based and the second fluid may be oil based as the situation demands during the well operations.

In another additional embodiment, the efficiency of the erosion or removal of the coating generated by a first fluid by the second fluid can be measured at predetermined intermediate concentrations of the first fluid and the second fluid under controlled hydrodynamic conditions under the influence of pressure and temperature. The electrical properties associated with this process are recorded dynamically to compare with the control properties with no coating in place and just the second fluid in the system.

The focus of the technique is to understand the contact time and shear rate requirements under pressure and temperature for approaching the wetting values of the test material in contact with the control pure fluid that is deployed for the cleanout operation under pressure and temperature. Wettability or wetting are surface characteristics and may be related to impedance, double layer capacitance, polarization resistance, or charge transfer resistance as accordingly modeled by a relevant equivalent electrical circuit.

In another embodiment, the method can additionally include the step of adjusting or optimizing the design composition of the downhole fluid to be contacted with the solid surface in the well based on the wettability or wetting of the test material in the test fluid.

In an embodiment, the method can further include a step of introducing a well fluid into the well, wherein the well fluid and conditions of introducing are adapted to achieve a downhole fluid and conditions of contacting the solid surface in the well to achieve a design wettability or wetting of the solid surface in the well.

CONCLUSION

Bulk conductivity information alone is insufficient to determine surface wettability or wetting.

Contact angle measurements are not feasible to be carried out with particulate-laden fluids. Moreover, contact angle measurement is an analytical technique that needs sophisticated tensiometers or goniometers.

Visual techniques like imaging to measure contact angle have been attempted but are not easily made quantitative.

The dye method demonstrated qualitative changes in surface wetting. Attempts were made to quantify using an imaging technique. However, curved surfaces could not be analyzed using this method. Repeatability could not be confirmed on curved surfaces because of high errors in imaging and image processing techniques and interpretation. This technique is not in-situ as the tested surface needed to be taken out of the solution to take photographs.

The disclosed invention provides an opportunity to carry out measurements using a non-invasive technique and quantify water- or oil-wettability or wetting at in-situ conditions. With continuous injection of surfactants and homogenization in the cell, using a mixing paddle, capacitances, and resistances can be monitored with respect to a control fluid to confirm the desired water wettability or wetting.

The methods can be used in surfactant package optimization to render water wet surfaces at downhole conditions.

In some applications, the methods can be used to provide increased probability of achieving full cement shear bond strength and better correlation with cement bond logs.

Prior lab testing using this technique and job execution in the field as designed can decrease the probability of micro annulus development and loss of interfacial bond during the lifecycle of the well and hence improves long-term zonal isolation.

This process can be carried out at HPHT by varying the type of formation or tubular surface experienced downhole, varying surface roughness, mill varnished, polished, corroded, etc.

Therefore, the present invention is well adapted to attain the ends and advantages mentioned as well as those that are inherent therein.

The particular embodiments disclosed above are illustrative only, as the present invention may be modified and practiced in different but equivalent manners apparent to those skilled in the art having the benefit of the teachings herein. It is, therefore, evident that the particular illustrative embodiments disclosed above may be altered or modified and all such variations are considered within the scope and spirit of the present invention.

The various elements or steps according to the disclosed elements or steps can be combined advantageously or practiced together in various combinations or sub-combinations of elements or sequences of steps to increase the efficiency and benefits that can be obtained from the invention.

The invention illustratively disclosed herein suitably may be practiced in the absence of any element or step that is not specifically disclosed or claimed.

Furthermore, no limitations are intended to the details of construction, composition, design, or steps herein shown, other than as described in the claims.

What is claimed is:

1. An apparatus comprising:
   a chamber having a first surface and a second surface, wherein the first surface contains a first bulk fluid; wherein the chamber contains a second bulk fluid; electrical insulation disposed between the first surface and the second surface;
   a shearing mechanism, wherein the shearing mechanism is operable to apply a shear between the second bulk fluid and the first surface at a shear rate, wherein the shear rate is nominally equivalent to an expected shear rate representative of wellbore conditions; and
   an electrical impedance spectroscopy tool operable to measure the wetness of the first surface.

2. The apparatus of claim 1, wherein the first surface is curved.

3. The apparatus of claim 1, wherein the second bulk fluid comprises a surfactant.

4. The apparatus of claim 1, wherein the second bulk fluid comprises a solid particulate.

5. The apparatus of claim 1, wherein the second bulk fluid comprises a foam.

6. The apparatus of claim 1, wherein the first bulk fluid is oleaginous.

7. The apparatus of claim 1, wherein the first bulk fluid is a dielectric.

8. The apparatus of claim 1, wherein the second bulk fluid comprises water.

9. The apparatus of claim 1, wherein the second bulk fluid comprises an electrolyte.

10. The apparatus of claim 1, wherein the first surface comprises a first electrode.

11. The apparatus of claim 1, wherein the second surface comprises a second electrode.

12. The apparatus of claim 1, wherein the chamber is disposed between a metallic tube and a borehole.

13. The apparatus of claim 1, further comprising an alternating electrical potential source operatively connected between the first surface and the second surface.

14. The apparatus of claim 1, further comprising a heating device operable to change the temperature of the second bulk fluid to a design temperature.

15. A method comprising:
    providing a chamber having a first surface and a second surface, wherein the first surface contains a first bulk fluid, and wherein the chamber contains a second bulk fluid;
    disposing electrical insulation between the first surface and the second surface;
    providing a shearing mechanism;
    applying a shear between the second bulk fluid and the first surface at a shear rate, wherein the shear rate is nominally equivalent to an expected shear rate representative of wellbore conditions; and
    measuring the wetness of the first surface with an electrical impedance spectroscopy tool.

16. The method of claim 15, wherein the first surface is curved.

17. The method of claim 15, wherein the second bulk fluid comprises a surfactant.

18. The method of claim 15, wherein the second bulk fluid comprises a solid particulate.

19. The method of claim 15, wherein the second bulk fluid comprises a foam.

* * * * *